(12) United States Patent
Trieu

(10) Patent No.: US 9,011,494 B2
(45) Date of Patent: Apr. 21, 2015

(54) COMPOSITE VERTEBRAL ROD SYSTEM AND METHODS OF USE

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 924 days.

(21) Appl. No.: 12/566,133

(22) Filed: Sep. 24, 2009

(65) Prior Publication Data

US 2011/0071570 A1    Mar. 24, 2011

(51) Int. Cl.
*A61B 17/70* (2006.01)
*A61B 19/00* (2006.01)

(52) U.S. Cl.
CPC .......... *A61B 17/7026* (2013.01); *A61B 17/7011* (2013.01); *A61B 17/7031* (2013.01); *A61B 2019/304* (2013.01)

(58) Field of Classification Search
CPC .................................. A61B 17/7019–17/7031
USPC .................. 606/246, 254–255, 257, 261–263
See application file for complete search history.

(56) References Cited

U.S. PATENT DOCUMENTS

| | | | |
|---|---|---|---|
| 4,694,881 A | 9/1987 | Busk | |
| 4,694,882 A | 9/1987 | Busk | |
| 4,743,260 A | 5/1988 | Burton | |
| 4,781,183 A | 11/1988 | Casey et al. | |
| 5,040,589 A | 8/1991 | Bradley et al. | |
| 5,064,463 A | 11/1991 | Ciomek | |
| 5,092,866 A | 3/1992 | Breard et al. | |
| 5,108,399 A | 4/1992 | Eitenmuller et al. | |
| 5,180,393 A | 1/1993 | Commarmond | |
| 5,282,863 A | 2/1994 | Burton | |
| 5,375,823 A | 12/1994 | Navas | |
| 5,415,661 A | 5/1995 | Holmes | |
| 5,423,816 A | 6/1995 | Lin | |
| 5,480,401 A | 1/1996 | Navas | |
| 5,540,688 A | 7/1996 | Navas | |
| 5,562,737 A | 10/1996 | Graf | |
| 5,577,546 A | 11/1996 | Kjar et al. | |
| 5,584,834 A | 12/1996 | Errico et al. | |
| 5,645,599 A | 7/1997 | Samani | |
| 5,672,175 A | 9/1997 | Martin | |

(Continued)

FOREIGN PATENT DOCUMENTS

FR     WO 2008/000944 A2 * 1/2008
FR     WO 2008/000944 A2 * 1/2008 ............. A61B 17/70

(Continued)

OTHER PUBLICATIONS

International Search Report and Written Opinion for US Application PCT/US2010/050035 mailed on Dec. 15, 2010.

*Primary Examiner* — Mary Hoffman
*Assistant Examiner* — Michelle C Eckman

(57) ABSTRACT

A vertebral rod includes a first elongated section including a first material having a first modulus of elasticity and a second elongated section including a second material having a second modulus of elasticity. A first intermediate section is disposed between the first section and the second section, and includes a third material having a third modulus of elasticity. The intermediate section has an arcuate inner surface that defines a cavity and an open end. The first modulus and the second modulus are each greater than the third modulus such that the first and second sections provide a reinforced configuration of the vertebral rod and the intermediate section has a relatively flexible configuration.

15 Claims, 7 Drawing Sheets

(56) References Cited

U.S. PATENT DOCUMENTS

| | | | |
|---|---|---|---|
| 5,704,936 A | 1/1998 | Mazel | |
| 5,733,284 A | 3/1998 | Martin | |
| 5,848,350 A | 12/1998 | Bulgar | |
| 5,961,516 A | 10/1999 | Graf | |
| 5,989,493 A | 11/1999 | La Salle et al. | |
| 5,993,448 A | 11/1999 | Remmler | |
| 5,993,507 A | 11/1999 | Baum et al. | |
| 6,093,201 A | 7/2000 | Cooper et al. | |
| 6,206,883 B1 | 3/2001 | Tunc | |
| 6,241,730 B1 | 6/2001 | Alby | |
| 6,248,106 B1 | 6/2001 | Ferree | |
| 6,267,764 B1* | 7/2001 | Elberg | 606/255 |
| 6,293,949 B1 | 9/2001 | Justis et al. | |
| 6,296,643 B1 | 10/2001 | Hopf et al. | |
| 6,298,901 B1 | 10/2001 | Sakamoto et al. | |
| 6,342,055 B1 | 1/2002 | Eisermann et al. | |
| 6,350,328 B1 | 2/2002 | Hostetler | |
| 6,402,750 B1 | 6/2002 | Atkinson et al. | |
| 6,440,169 B1 | 8/2002 | Elberg et al. | |
| 6,461,359 B1 | 10/2002 | Tribus et al. | |
| 6,470,956 B2 | 10/2002 | Sakamoto et al. | |
| 6,478,842 B1 | 11/2002 | Gressel et al. | |
| 6,547,790 B2 | 4/2003 | Harkey, III et al. | |
| 6,572,619 B2 | 6/2003 | Santilli | |
| 6,572,653 B1 | 6/2003 | Simonson | |
| 6,599,290 B2 | 7/2003 | Bailey et al. | |
| 6,613,051 B1 | 9/2003 | Luke et al. | |
| 6,616,669 B2 | 9/2003 | Ogilvie et al. | |
| 6,619,370 B2 | 9/2003 | Sakamoto et al. | |
| 6,626,904 B1 | 9/2003 | Jammet et al. | |
| 6,645,207 B2 | 11/2003 | Dixon et al. | |
| 6,669,898 B2 | 12/2003 | Gressel et al. | |
| 6,706,044 B2 | 3/2004 | Kuslich et al. | |
| 6,730,093 B2 | 5/2004 | Saint Martin | |
| 6,740,088 B1 | 5/2004 | Kozak et al. | |
| 6,749,614 B2 | 6/2004 | Teitelbaum et al. | |
| 6,761,719 B2 | 7/2004 | Justis et al. | |
| 6,770,075 B2 | 8/2004 | Howland | |
| 6,783,527 B2 | 8/2004 | Drewry et al. | |
| 6,790,252 B2 | 9/2004 | Smith et al. | |
| 6,835,205 B2 | 12/2004 | Atkinson et al. | |
| 6,838,046 B2 | 1/2005 | Lu et al. | |
| 6,843,790 B2 | 1/2005 | Ferree | |
| 6,858,029 B2 | 2/2005 | Yeh | |
| 6,860,316 B2 | 3/2005 | Wu et al. | |
| 6,966,910 B2 | 11/2005 | Ritland | |
| 6,986,771 B2 | 1/2006 | Paul et al. | |
| 6,989,011 B2 | 1/2006 | Paul et al. | |
| 6,991,632 B2 | 1/2006 | Ritland | |
| 7,018,379 B2 | 3/2006 | Drewry et al. | |
| 7,029,475 B2 | 4/2006 | Panjabi | |
| 7,066,957 B2 | 6/2006 | Graf | |
| 7,083,621 B2 | 8/2006 | Shaolian et al. | |
| 7,083,622 B2 | 8/2006 | Simonson | |
| 7,125,410 B2 | 10/2006 | Freudiger | |
| 7,137,985 B2 | 11/2006 | Jahng | |
| 7,207,992 B2 | 4/2007 | Ritland | |
| 7,229,441 B2 | 6/2007 | Trieu et al. | |
| 7,282,065 B2 | 10/2007 | Kirschman | |
| 7,285,121 B2 | 10/2007 | Braun et al. | |
| 7,291,150 B2 | 11/2007 | Graf | |
| 7,297,146 B2 | 11/2007 | Braun et al. | |
| 7,326,210 B2 | 2/2008 | Jahng et al. | |
| 7,329,258 B2 | 2/2008 | Studer | |
| 7,335,200 B2 | 2/2008 | Carli | |
| 7,338,525 B2 | 3/2008 | Ferree | |
| 7,361,196 B2 | 4/2008 | Fallin et al. | |
| 7,377,921 B2 | 5/2008 | Studer et al. | |
| 7,476,238 B2 | 1/2009 | Panjabi | |
| 7,556,639 B2 | 7/2009 | Rothman et al. | |
| 7,559,942 B2 | 7/2009 | Paul et al. | |
| 7,578,849 B2 | 8/2009 | Trieu | |
| 7,601,166 B2 | 10/2009 | Biedermann et al. | |
| 7,604,653 B2 | 10/2009 | Kitchen | |
| 7,604,654 B2 | 10/2009 | Fallin et al. | |
| 7,815,663 B2* | 10/2010 | Trieu | 606/254 |
| 2002/0133155 A1 | 9/2002 | Ferree | |
| 2003/0109880 A1 | 6/2003 | Shirado et al. | |
| 2003/0114853 A1 | 6/2003 | Burgess et al. | |
| 2003/0120280 A1 | 6/2003 | Roller et al. | |
| 2003/0171749 A1 | 9/2003 | Le Couedic et al. | |
| 2003/0220643 A1 | 11/2003 | Ferree | |
| 2004/0002708 A1 | 1/2004 | Ritland | |
| 2004/0006343 A1 | 1/2004 | Sevrain | |
| 2004/0015166 A1 | 1/2004 | Gorek | |
| 2004/0049189 A1 | 3/2004 | Le Couedic et al. | |
| 2004/0049190 A1 | 3/2004 | Biedermann et al. | |
| 2004/0054411 A1 | 3/2004 | Kelly et al. | |
| 2004/0097931 A1 | 5/2004 | Mitchell | |
| 2004/0143264 A1 | 7/2004 | McAfee | |
| 2004/0147928 A1 | 7/2004 | Landry et al. | |
| 2004/0172024 A1 | 9/2004 | Gorek | |
| 2004/0215190 A1 | 10/2004 | Nguyen et al. | |
| 2004/0215192 A1 | 10/2004 | Justis et al. | |
| 2004/0267260 A1 | 12/2004 | Mack et al. | |
| 2005/0010298 A1 | 1/2005 | Zucherman et al. | |
| 2005/0038432 A1 | 2/2005 | Shaolian et al. | |
| 2005/0049708 A1 | 3/2005 | Atkinson et al. | |
| 2005/0055244 A1 | 3/2005 | Mullan et al. | |
| 2005/0065515 A1 | 3/2005 | Jahng | |
| 2005/0065516 A1 | 3/2005 | Jahng | |
| 2005/0085814 A1 | 4/2005 | Sherman et al. | |
| 2005/0085815 A1 | 4/2005 | Harms et al. | |
| 2005/0113927 A1 | 5/2005 | Malek | |
| 2005/0124991 A1 | 6/2005 | Jahng | |
| 2005/0131407 A1 | 6/2005 | Sicvol et al. | |
| 2005/0143737 A1 | 6/2005 | Pafford et al. | |
| 2005/0143823 A1 | 6/2005 | Boyd et al. | |
| 2005/0149020 A1 | 7/2005 | Jahng | |
| 2005/0149023 A1 | 7/2005 | Ritland | |
| 2005/0154390 A1 | 7/2005 | Biedermann et al. | |
| 2005/0165396 A1 | 7/2005 | Fortin et al. | |
| 2005/0171540 A1 | 8/2005 | Lim et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0177164 A1 | 8/2005 | Walters et al. | |
| 2005/0182400 A1 | 8/2005 | White | |
| 2005/0182401 A1 | 8/2005 | Timm et al. | |
| 2005/0182409 A1 | 8/2005 | Callahan et al. | |
| 2005/0203511 A1 | 9/2005 | Wilson-MacDonald et al. | |
| 2005/0203513 A1 | 9/2005 | Jahng et al. | |
| 2005/0203514 A1 | 9/2005 | Jahng et al. | |
| 2005/0203519 A1 | 9/2005 | Harms et al. | |
| 2005/0209694 A1 | 9/2005 | Loeb | |
| 2005/0261685 A1 | 11/2005 | Fortin et al. | |
| 2005/0261686 A1 | 11/2005 | Paul | |
| 2005/0277922 A1 | 12/2005 | Trieu et al. | |
| 2005/0277934 A1 | 12/2005 | Vardiman | |
| 2005/0288670 A1 | 12/2005 | Panjabi et al. | |
| 2005/0288672 A1 | 12/2005 | Ferree | |
| 2006/0004367 A1 | 1/2006 | Alamin et al. | |
| 2006/0009768 A1 | 1/2006 | Ritland | |
| 2006/0009846 A1 | 1/2006 | Trieu et al. | |
| 2006/0036240 A1 | 2/2006 | Colleran et al. | |
| 2006/0064090 A1* | 3/2006 | Park | 606/61 |
| 2006/0084982 A1 | 4/2006 | Kim | |
| 2006/0084984 A1 | 4/2006 | Kim | |
| 2006/0084987 A1 | 4/2006 | Kim | |
| 2006/0084991 A1 | 4/2006 | Borgstrom et al. | |
| 2006/0089645 A1 | 4/2006 | Eckman | |
| 2006/0142758 A1 | 6/2006 | Petit | |
| 2006/0142760 A1 | 6/2006 | McDonnell | |
| 2006/0184171 A1* | 8/2006 | Biedermann et al. | 606/61 |
| 2006/0189985 A1 | 8/2006 | Lewis | |
| 2006/0195093 A1 | 8/2006 | Jahng | |
| 2006/0212033 A1 | 9/2006 | Rothman et al. | |
| 2006/0229608 A1* | 10/2006 | Foster et al. | 606/61 |
| 2006/0240533 A1 | 10/2006 | Sengupta et al. | |
| 2006/0247632 A1 | 11/2006 | Winslow et al. | |
| 2006/0247637 A1 | 11/2006 | Colleran et al. | |
| 2006/0247638 A1 | 11/2006 | Trieu et al. | |
| 2006/0264935 A1 | 11/2006 | White | |
| 2006/0264937 A1 | 11/2006 | White | |

(56) References Cited

U.S. PATENT DOCUMENTS

| | | |
|---|---|---|
| 2006/0271048 A1 | 11/2006 | Thramann |
| 2006/0276247 A1 | 12/2006 | Martinez |
| 2006/0276790 A1 | 12/2006 | Dawson et al. |
| 2006/0282080 A1 | 12/2006 | Albert et al. |
| 2006/0293657 A1 | 12/2006 | Hartmann |
| 2007/0005062 A1 | 1/2007 | Lange et al. |
| 2007/0016190 A1 | 1/2007 | Martinez et al. |
| 2007/0016193 A1 | 1/2007 | Ritland |
| 2007/0016200 A1 | 1/2007 | Jackson |
| 2007/0016201 A1 | 1/2007 | Freudiger |
| 2007/0043356 A1 | 2/2007 | Timm et al. |
| 2007/0049936 A1 | 3/2007 | Colleran et al. |
| 2007/0049937 A1 | 3/2007 | Matthis et al. |
| 2007/0055247 A1 | 3/2007 | Jahng |
| 2007/0073289 A1 | 3/2007 | Kwak et al. |
| 2007/0088359 A1 | 4/2007 | Woods et al. |
| 2007/0100341 A1 | 5/2007 | Reglos et al. |
| 2007/0118122 A1 | 5/2007 | Butler et al. |
| 2007/0123865 A1 | 5/2007 | Schlapfer et al. |
| 2007/0123871 A1 | 5/2007 | Jahng |
| 2007/0129729 A1 | 6/2007 | Petit et al. |
| 2007/0190230 A1* | 8/2007 | Trieu et al. ............... 427/2.24 |
| 2007/0191832 A1* | 8/2007 | Trieu ............................ 606/61 |
| 2007/0191846 A1 | 8/2007 | Bruneau et al. |
| 2007/0198088 A1 | 8/2007 | Biedermann et al. |
| 2007/0203446 A1 | 8/2007 | Biedermann et al. |
| 2007/0213719 A1 | 9/2007 | Hudgins et al. |
| 2007/0225710 A1 | 9/2007 | Jahng et al. |
| 2007/0233064 A1 | 10/2007 | Holt |
| 2007/0270814 A1 | 11/2007 | Lim et al. |
| 2007/0270821 A1 | 11/2007 | Trieu et al. |
| 2007/0270837 A1 | 11/2007 | Eckhardt et al. |
| 2007/0270838 A1 | 11/2007 | Bruneau et al. |
| 2007/0270860 A1 | 11/2007 | Jackson |
| 2007/0276380 A1 | 11/2007 | Jahng et al. |
| 2007/0276500 A1 | 11/2007 | Zucherman et al. |
| 2007/0288008 A1 | 12/2007 | Park |
| 2007/0288011 A1 | 12/2007 | Logan |
| 2007/0288093 A1 | 12/2007 | Le Couedic et al. |
| 2007/0293862 A1 | 12/2007 | Jackson |
| 2008/0021459 A1 | 1/2008 | Lim |
| 2008/0027549 A1 | 1/2008 | Kirschman |
| 2008/0033435 A1 | 2/2008 | Studer et al. |
| 2008/0039943 A1 | 2/2008 | Le Couedic |
| 2008/0045951 A1 | 2/2008 | Fanger et al. |
| 2008/0051787 A1 | 2/2008 | Remington et al. |
| 2008/0065071 A1 | 3/2008 | Park |
| 2008/0097431 A1 | 4/2008 | Vessa |
| 2008/0097434 A1* | 4/2008 | Moumene et al. ............ 606/61 |
| 2008/0125777 A1 | 5/2008 | Veldman et al. |
| 2008/0140076 A1 | 6/2008 | Jackson |
| 2008/0140122 A1 | 6/2008 | Bethell |
| 2008/0147122 A1 | 6/2008 | Jackson |
| 2008/0154307 A1 | 6/2008 | Colleran et al. |
| 2008/0154308 A1 | 6/2008 | Sherman et al. |
| 2008/0161854 A1 | 7/2008 | Bae et al. |
| 2008/0167687 A1 | 7/2008 | Colleran et al. |
| 2008/0172091 A1 | 7/2008 | Anderson |
| 2008/0177263 A1 | 7/2008 | Freedman et al. |
| 2008/0177316 A1 | 7/2008 | Bergeron et al. |
| 2008/0177317 A1 | 7/2008 | Jackson |
| 2008/0177320 A1 | 7/2008 | McBride |
| 2008/0177329 A1 | 7/2008 | Perez-Cruet et al. |
| 2008/0177331 A1 | 7/2008 | Perez-Cruet et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0215094 A1 | 9/2008 | Taylor |
| 2008/0221620 A1 | 9/2008 | Krause |
| 2008/0234739 A1 | 9/2008 | Hudgins et al. |
| 2008/0234744 A1 | 9/2008 | Zylber et al. |
| 2008/0255617 A1 | 10/2008 | Cho et al. |
| 2008/0262552 A1* | 10/2008 | Kim ............................ 606/276 |
| 2008/0262554 A1 | 10/2008 | Hayes et al. |
| 2008/0294195 A1 | 11/2008 | Egli et al. |
| 2008/0294197 A1 | 11/2008 | Egli et al. |
| 2008/0300633 A1 | 12/2008 | Jackson |
| 2008/0306450 A1 | 12/2008 | Martin |
| 2008/0306451 A1 | 12/2008 | Woehr et al. |
| 2008/0306452 A1 | 12/2008 | Crawford |
| 2008/0312694 A1 | 12/2008 | Peterman et al. |
| 2008/0319482 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0093819 A1 | 4/2009 | Joshi |
| 2009/0093845 A1* | 4/2009 | Hestad et al. ............... 606/254 |
| 2009/0093846 A1 | 4/2009 | Hestad |
| 2009/0099606 A1 | 4/2009 | Hestad et al. |
| 2009/0099607 A1 | 4/2009 | Fallin et al. |
| 2009/0105762 A1 | 4/2009 | Jackson |
| 2009/0112265 A1 | 4/2009 | Hudgins et al. |
| 2009/0118767 A1 | 5/2009 | Hestad et al. |
| 2009/0131981 A1 | 5/2009 | White |
| 2009/0163953 A1 | 6/2009 | Biedermann et al. |
| 2009/0163955 A1 | 6/2009 | Moumene et al. |
| 2009/0171395 A1 | 7/2009 | Jeon et al. |
| 2009/0192548 A1* | 7/2009 | Jeon et al. .................. 606/246 |
| 2009/0228043 A9 | 9/2009 | Egli et al. |
| 2009/0228044 A1 | 9/2009 | Jeon et al. |
| 2009/0228045 A1 | 9/2009 | Hayes et al. |
| 2010/0211104 A1* | 8/2010 | Moumene et al. ........... 606/257 |
| 2010/0222818 A1* | 9/2010 | Trieu et al. .................. 606/254 |
| 2010/0222820 A1* | 9/2010 | Trieu ............................ 606/255 |

FOREIGN PATENT DOCUMENTS

| | | | | |
|---|---|---|---|---|
| KR | 20-2003-0030651 | * | 1/2004 | ............ A61B 17/70 |
| WO | 2008000944 A2 | | 1/2008 | |

* cited by examiner

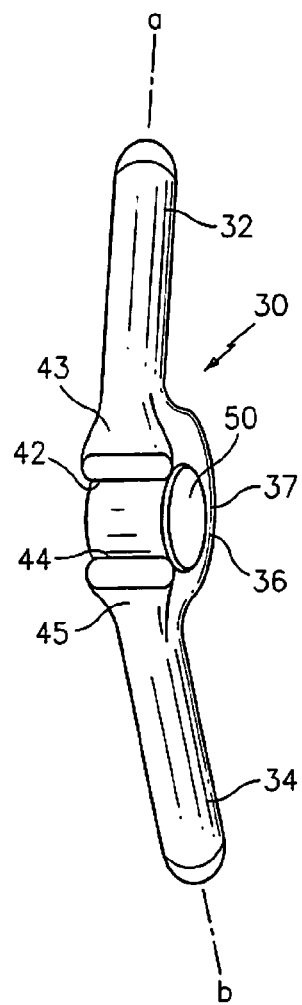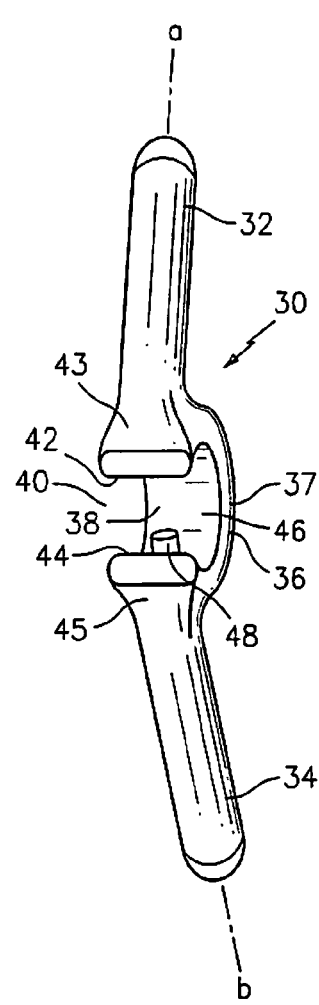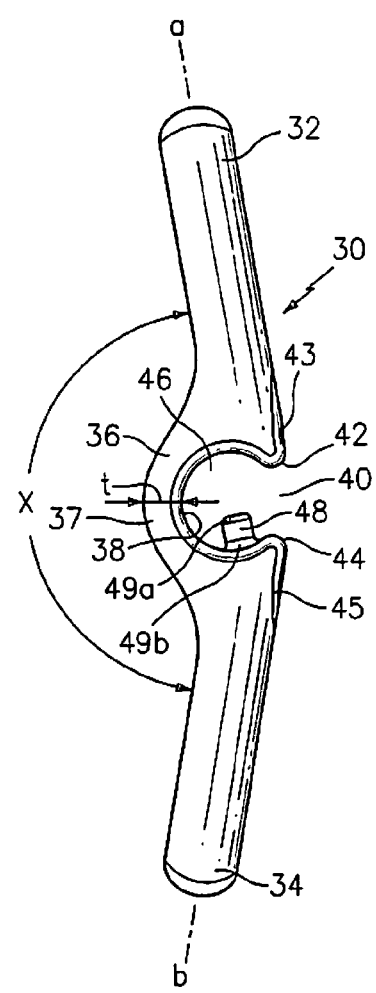
FIG. 1  FIG. 2  FIG. 3
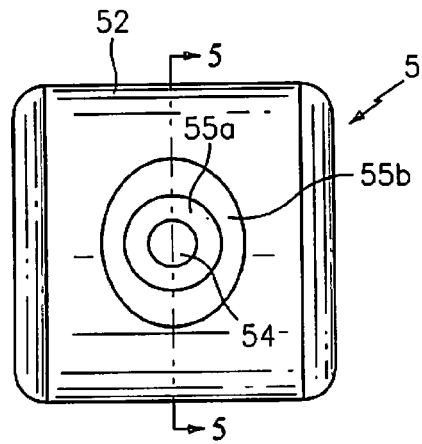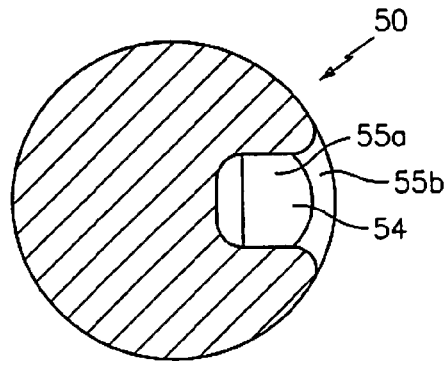
FIG. 4  FIG. 5

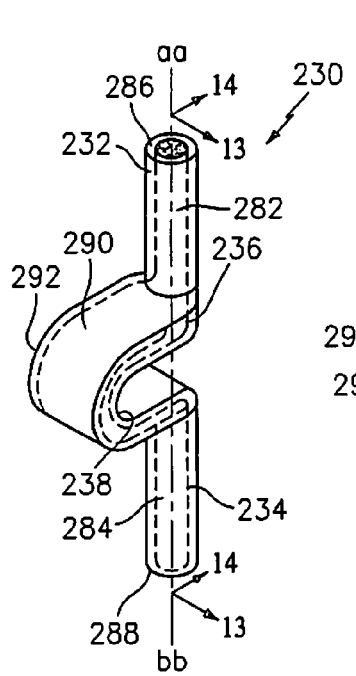
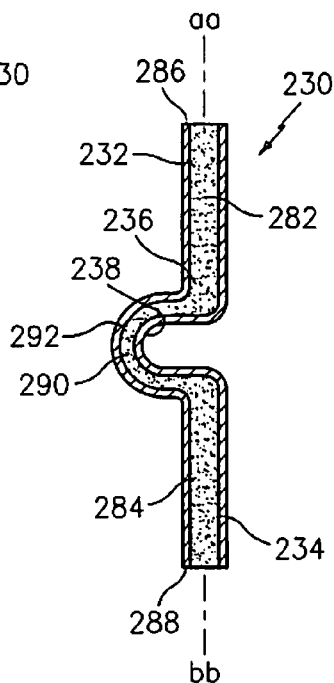
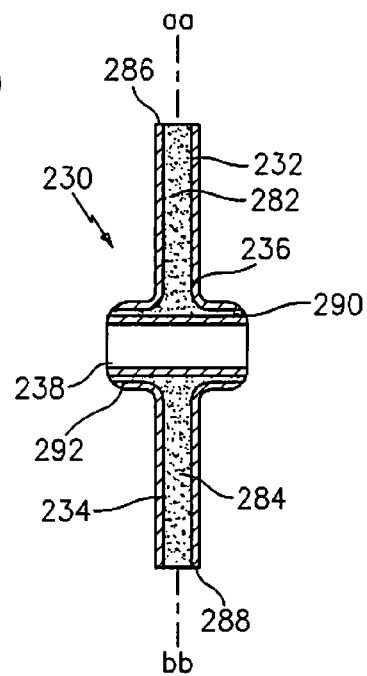
FIG. 12     FIG. 13     FIG. 14
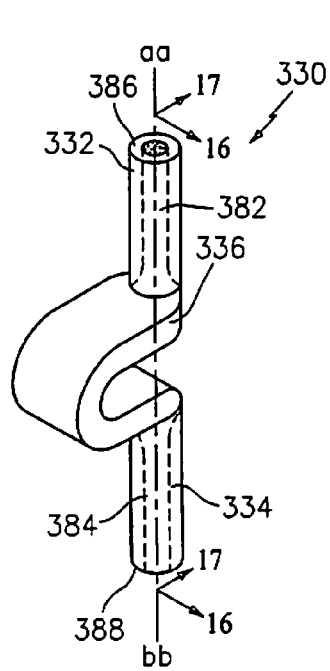
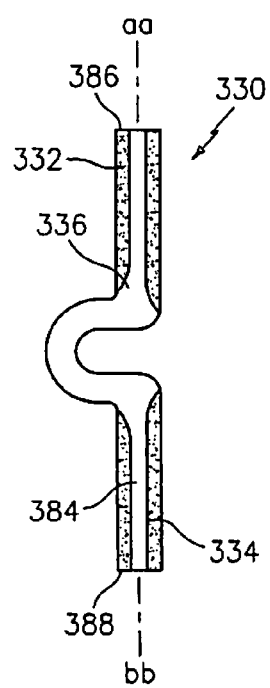
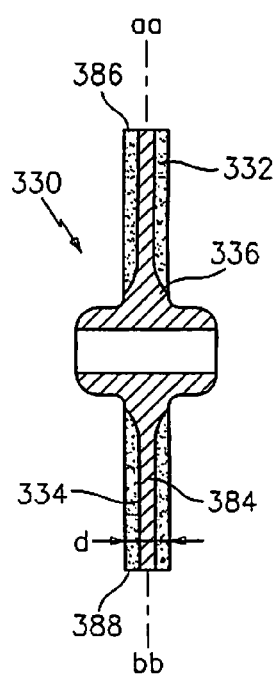
FIG. 15     FIG. 16     FIG. 17

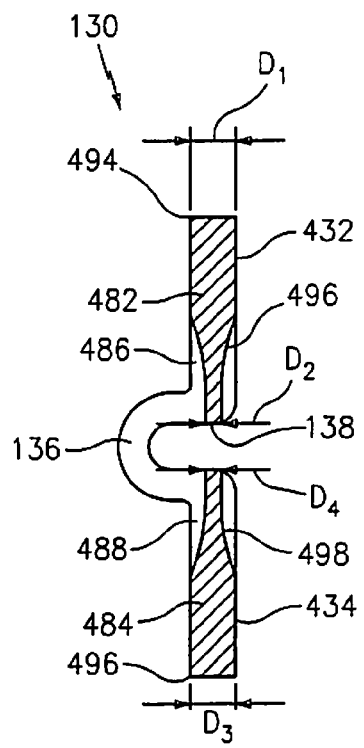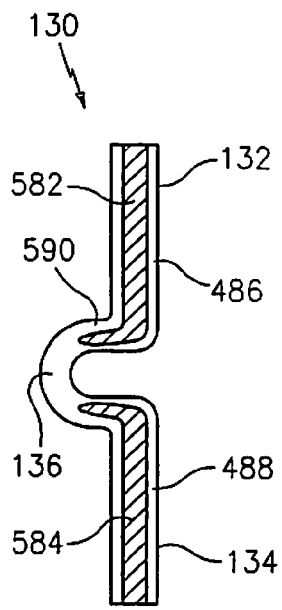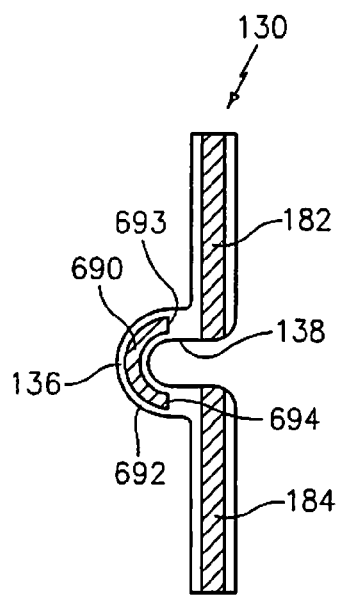
FIG. 18          FIG. 19          FIG. 20
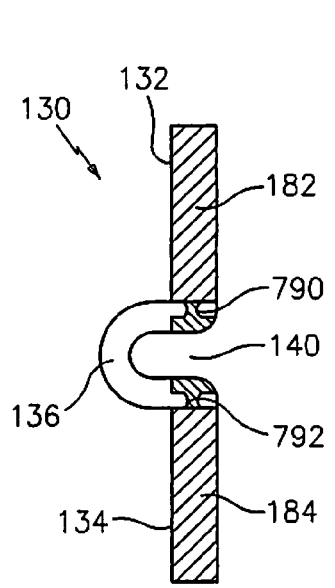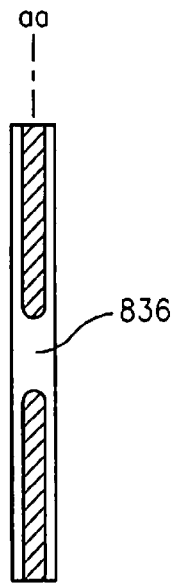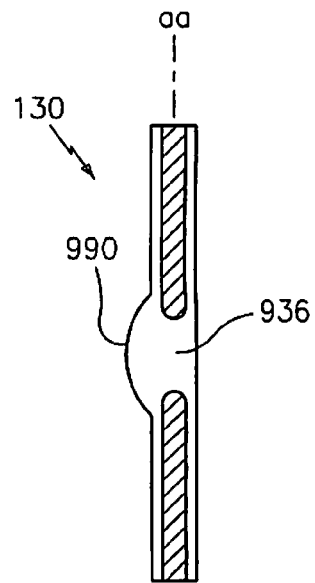
FIG. 21          FIG. 22          FIG. 23

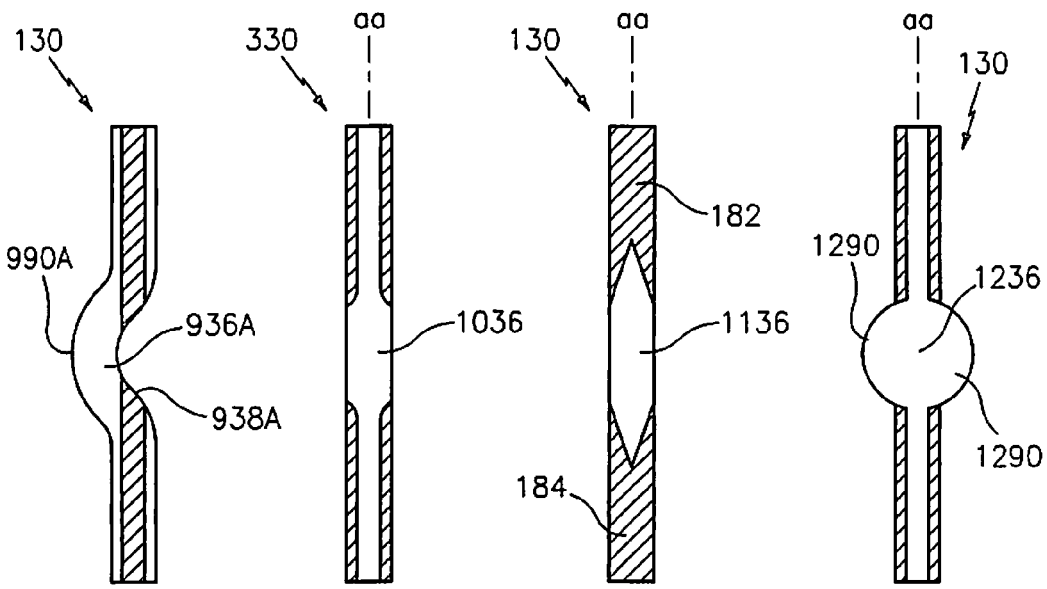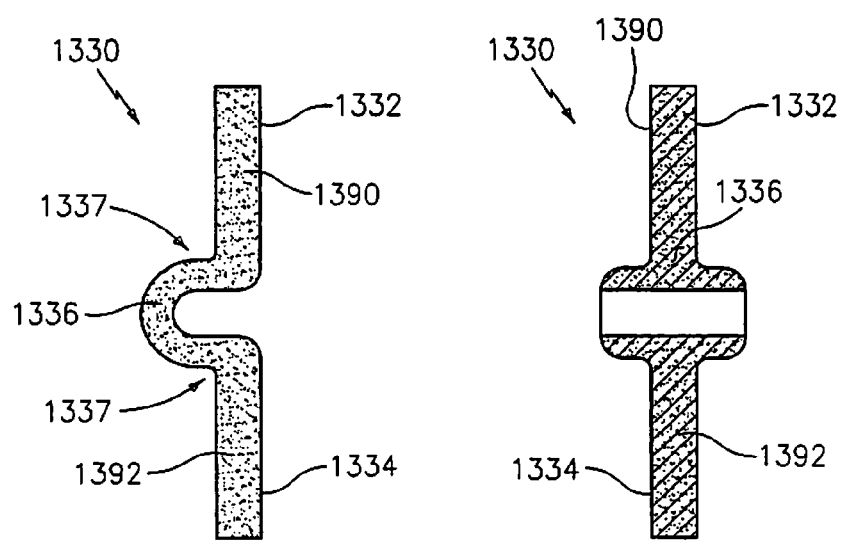

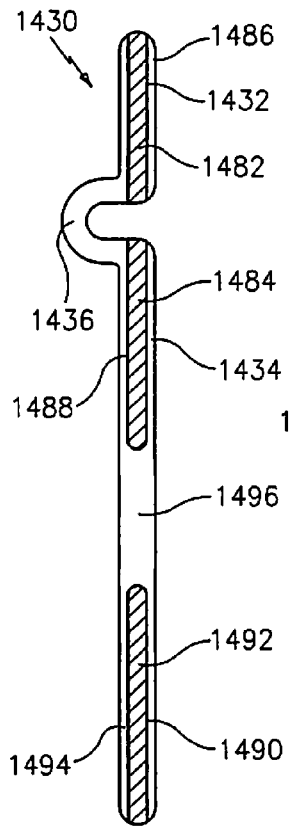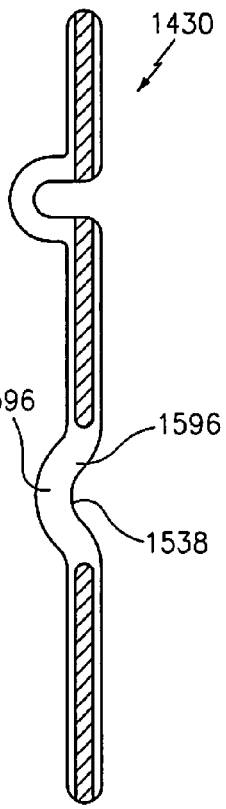
FIG. 30   FIG. 31
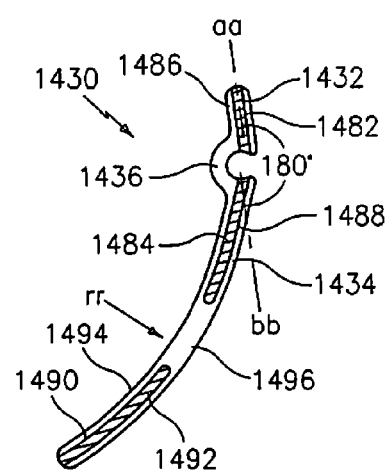
FIG. 30A
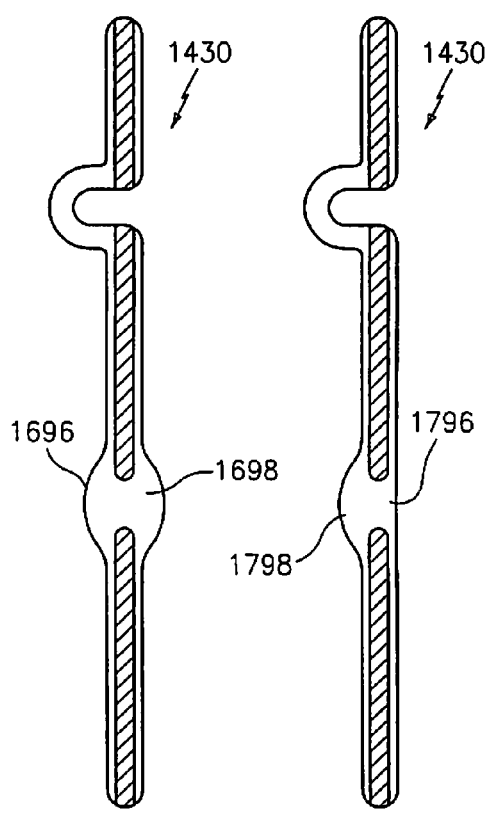
FIG. 32   FIG. 33

COMPOSITE VERTEBRAL ROD SYSTEM AND METHODS OF USE

TECHNICAL FIELD

The present disclosure generally relates to medical devices for the treatment of spinal disorders, and more particularly to a dynamic vertebral rod system, having flexion and extension capability, which provides stability while reducing stress on spinal elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders include discectomy, laminectomy, fusion and implantable prosthetics. As part of these surgical treatments, connecting elements such as vertebral rods are often used to provide stability to a treated region. During surgical treatment, one or more rods may be attached to the exterior of two or more vertebral members.

Rods redirect stresses away from a damaged or defective region while healing takes place to restore proper alignment and generally support the vertebral members. In some applications, rods are attached to the vertebral members without the use of implants or spinal fusion. Flexible connecting elements are also known that permit limited spinal motion of a spinal motion segment. Such flexible connecting elements can provide dynamic spinal support. While prior connecting elements have attempted to provide effective spinal stabilization, there remains a need for connecting elements that provide a dynamic stabilizing resistance to forces and permit motion of a spinal column segment(s) in flexion and extension while effectively stabilizing the spinal column segment(s) and the structural integrity of the connecting element.

Therefore, it would be desirable to provide a dynamic vertebral rod system, having flexion and extension capability, which provides stability while reducing stress on spinal elements. The present disclosure describes improvement over these prior art technologies.

SUMMARY OF THE INVENTION

Accordingly, a dynamic vertebral rod system is provided, having flexion and extension capability, which provides stability while reducing stress on spinal elements. The vertebral rod system can include a configuration to provide increased strength and stiffness to the rod while maintaining flexibility at selected portions of the rod. It is envisioned that the disclosed system may be employed as a posterior, anterior and/or lateral dynamic stabilization device. The components of the vertebral rod system are easily manufactured and assembled.

In one particular embodiment, in accordance with the principles of the present disclosure, a vertebral rod is provided. The vertebral rod includes a first elongated section including a first material having a first modulus of elasticity and a second elongated section including a second material having a second modulus of elasticity. A first intermediate section is disposed between the first section and the second section, and includes a third material having a third modulus of elasticity. The intermediate section having an arcuate inner surface that defines a cavity and an open end. The first modulus and the second modulus are each greater than the third modulus such that the first and second sections provide a reinforced configuration of the vertebral rod and the intermediate section has a relatively flexible configuration.

The first section may include an outer layer disposed about the first material. The outer layer is formed of a material having a modulus of elasticity that is less than the first modulus. The second section may include an outer layer disposed about the second material. The outer layer of the second section is formed of a material having a modulus of elasticity that is less than the second modulus.

Alternatively, at least a portion of the intermediate section includes a reinforcement portion having a modulus of elasticity that is greater than the third modulus. The third material is an outer layer disposed about the reinforcement portion. The reinforcement portion of the intermediate section can have an arcuate configuration. The reinforcement portion may connect the first material and the second material such that the first, second and intermediate sections are in a continuous reinforcement configuration of the vertebral rod.

The first section may include an elongated core formed of a material having a modulus of elasticity that is less than the first modulus. The first material is an outer layer disposed about the core. The second section may include an elongated core formed of a material having a modulus of elasticity that is less than the second modulus. The second material is an outer layer disposed about the core of the second section. The first material can be an elongated core having a cross section extending from a first end of the first section to the inner surface of the intermediate section. The core cross section comprises an outer diameter of the first section adjacent the first end and including a tapered portion with a reduced diameter, relative to the outer diameter, adjacent the inner surface.

The second material may be an elongated core having a cross section extending from a first end of the second section to the inner surface of the intermediate section. The core cross section of the second section comprises an outer diameter of the second section adjacent the first end of the second section and including a tapered portion with a reduced diameter, relative to the outer diameter of the second section, adjacent the inner surface.

Alternatively, the reinforcement portion of the intermediate section may be arcuately disposed about the inner surface and having a first end, the first end being spaced apart from the first material. The reinforcement portion of the intermediate section may have a second end that is spaced apart from the second material. The second intermediate section may include at least one lateral protuberance.

In another embodiment, the vertebral rod includes a first elongated section including an elongated core and an outer layer disposed about the core. At least one of the core and the outer layer are formed of a first material having a modulus of elasticity greater than 30 gigapascal (GPa). The other of the core and the outer layer is formed of a second material having a modulus of elasticity less than 20 GPa. A second elongated section includes an elongated core and an outer layer disposed about the core of the second section. At least one of the core of the second section and the outer layer is formed of the first material. The other of the core and the outer layer of the second section is formed of the second material. An intermediate section is disposed between the first section and the second section, and is formed of the second material. The intermediate section has an arcuate inner surface that defines a cavity and an open end of the intermediate section.

In another embodiment, the vertebral rod includes a third elongated section including a fourth material having a fourth modulus of elasticity. A second flexible intermediate section is disposed between the second section and the third section. The fourth modulus is greater than the third modulus.

BRIEF DESCRIPTION OF THE DRAWINGS

The present disclosure will become more readily apparent from the specific description accompanied by the following drawings, in which:

FIG. 1 is a perspective view of one particular embodiment of the vertebral rod system in accordance with the principles of the present disclosure;

FIG. 2 is a perspective view of a vertebral rod of the vertebral rod system shown in FIG. 1;

FIG. 3 is a side plan view of the vertebral rod shown in FIG. 2;

FIG. 4 is a perspective view of a resistance member of the vertebral rod system shown in FIG. 1;

FIG. 5 is a side, cross-section view of the resistance member taken along line 5-5 in FIG. 4;

FIG. 12 is a side perspective view of an alternate embodiment of the vertebral rod shown in FIG. 8;

FIG. 13 is a side cross-section view of the vertebral rod taken along line 13-13 shown in FIG. 12;

FIG. 14 is a front cross-section view of the vertebral rod taken along line 14-14 shown in FIG. 12;

FIG. 15 is a side perspective view of an alternate embodiment of the vertebral rod shown in FIG. 8;

FIG. 16 is a side cross-section view of the vertebral rod taken along line 16-16 shown in FIG. 15;

FIG. 17 is a front cross-section view of the vertebral rod taken along line 17-17 shown in FIG. 15;

FIG. 18 is a side cross-section view of another alternate embodiment of the vertebral rod shown in FIG. 8;

FIG. 19 is a side cross-section view of another alternate embodiment of the vertebral rod shown in FIG. 8;

FIG. 20 is a side cross-section view of another alternate embodiment of the vertebral rod shown in FIG. 8;

FIG. 21 is a side cross-section view of another alternate embodiment of the vertebral rod shown in FIG. 8;

FIG. 22 is a side cross-section view of another alternate embodiment of the vertebral rod shown in FIG. 8;

FIG. 23 is a side cross-section view of another alternate embodiment of the vertebral rod shown in FIG. 8;

FIG. 24 is a side cross-section view of another alternate embodiment of the vertebral rod shown in FIG. 8;

FIG. 25 is a side cross-section view of another alternate embodiment of the vertebral rod shown in FIG. 8;

FIG. 26 is a side cross-section view of another alternate embodiment of the vertebral rod shown in FIG. 8;

FIG. 27 is a side cross-section view of another alternate embodiment of the vertebral rod shown in FIG. 8;

FIG. 28 is a side cross section view of another alternate embodiment of the vertebral rod shown in FIG. 8;

FIG. 29 is a front cross section view of the vertebral rod shown in FIG. 28;

FIG. 30 is a side cross section view of another alternate embodiment of the vertebral rod shown in FIG. 2;

FIG. 30A is a side cross section view of an alternate embodiment of the vertebral rod shown in FIG. 30;

FIG. 31 is a side cross section view of another alternate embodiment of the vertebral rod shown in FIG. 2;

FIG. 32 is a side cross section view of another alternate embodiment of the vertebral rod shown in FIG. 2; and FIG. 33 is a side cross section view of another alternate embodiment of the vertebral rod shown in FIG. 2.

Like reference numerals indicate similar parts throughout the figures.

DETAILED DESCRIPTION OF THE INVENTION

Figure 6:
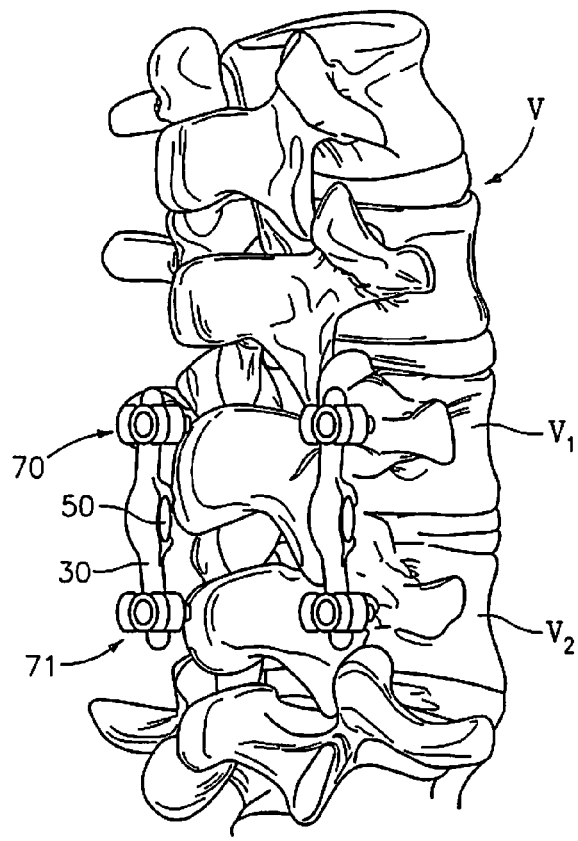
FIG. 6 is a perspective view of a vertebral rod system of the present disclosure attached to vertebrae.

The exemplary embodiments of the vertebral rod system and methods of use disclosed are discussed in terms of medical devices for the treatment of spinal disorders and more particularly, in terms of a dynamic vertebral rod system having flexion and extension capability. It is envisioned that the vertebral rod system and methods of use disclosed provide stability and maintains structural integrity while reducing stress on spinal elements. It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is further envisioned that the present disclosure may be employed with surgical treatments including open surgery and minimally invasive procedures, of such disorders, such as, for example, discectomy, laminectomy, fusion, bone graft and implantable prosthetics. It is contemplated that the present disclosure may be employed with other osteal and bone related applications, including those associated with diagnostics and therapeutics. It is further contemplated that the disclosed vertebral rod system may be employed in a surgical treatment with a patient in a prone or supine position, employing a posterior, lateral or anterior approach. The present disclosure may be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a vertebral rod system, related components and exemplary methods of employing the vertebral rod system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there are illustrated components of a vertebral rod system in accordance with the principles of the present disclosure.

The components of the vertebral rod system are fabricated from materials suitable for medical applications, including metals, polymers, ceramics, biocompatible materials and/or their composites, depending on the particular application and/or preference of a medical practitioner. For example, a vertebral rod, discussed below, of the vertebral rod system can be fabricated from materials such as commercially pure titanium, titanium alloys, super-elastic titanium alloys, cobalt-chrome alloys, stainless steel alloys, thermoplastics such as polyaryletherketone (PAEK) including polyetheretherketone (PEEK), polyetherketoneketone (PEKK) and polyetherketone (PEK), carbon fiber reinforced PEEK composites, PEEK-$BaSO_4$ composites, biocompatible materials such as polymers including plastics, metals, ceramics and composites thereof, rigid polymers including polyphenylene, polyamide, polyimide, polyetherimide, polyethylene, polyurethane, epoxy, silicone; and different sections of the rod may have alternative material composites to achieve various desired characteristics such as strength, rigidity, elasticity, compliance biomechanical performance, durability and radiolucency or imaging preference.

For example, the vertebral rod can be formed of two or more materials. In one embodiment, elongated rod sections can be fabricated from carbon-reinforced PEEK and an intermediate section can be fabricated from PEEK. In another embodiment, elongated rod sections are fabricated from PEEK and an intermediate section is fabricated from carbon-reinforced PEEK. In another embodiment, alternate materials may be employed in a radial direction of a vertebral rod such that stiff materials such as metals or other composites are used in a core of the rod sections and an outer sheet of lower modulus of elasticity polymeric material is used in the outer radial portion of the rod sections, or vice versa. In another embodiment employing a composite material similar to those described, the elongated rod sections can have a cylindrical geometry and the intermediate section can have a rectangular or oblong geometry. See also, for example, the material configurations and manufacturing methods described in U.S. Patent Application Publication No. 2006/0247638 the contents of which being incorporated by reference herein in its entirety. It is envisioned that the rod or device can be manufactured via various methods including machining, casting, injection-molding, insert-molding, overmolding, compression molding, transfer molding, co-extrusion, pultrusion, dip-coating, spray-coating, powder-coating, porous-coating, and their combinations.

As a further example, a resistance member of the vertebral rod system may be fabricated from materials such as silicone, polyurethane, silicone-polyurethane copolymers, polymeric rubbers, polyolefin rubbers, hydrogels, semi-rigid and rigid materials, and biocompatible materials such as elastomers, rubbers, thermoplastic elastomers, thermoset elastomers, elastomeric composites and plastics. It is envisioned that the rod sections can be manufactured from, for example, machining and milling from a solid stock material and/or injection molding. The resistance member can be manufactured from, for example, machining and milling, extrusion and die cutting, injection molding, transfer molding and/or cast molding. One skilled in the art, however, will realize that such materials and fabrication methods suitable for assembly and manufacture, in accordance with the present disclosure, would be appropriate.

The vertebral rod system is configured for attachment to vertebrae (as shown, for example, in FIG. 6) during surgical treatment of a spinal disorder, examples of which are discussed herein. See also, for example, the vertebral rod systems and methods described in U.S. patent application Ser. No. 12/192,606 (prior filed Medtronic patent application, P0032163.00), the contents of which being incorporated by reference herein in its entirety. The vertebral rod system has a vertebral rod 30, which includes a first elongated section, such as, for example, upper section 32 that defines a longitudinal axis a. A second elongated section, such as, for example, lower section 34 defines a longitudinal axis b.

An intermediate section 36 is connected with sections 32, 34 and disposed therebetween as a joining section of the components of vertebral rod 30. It is envisioned that the components of vertebral rod 30 may be monolithically formed, integrally connected or arranged with attaching elements. Intermediate section 36 is flexible relative to sections 32, 34, and is configured to provide resistance to movement of sections 32, 34. It is envisioned that intermediate section 36 may provide increasing, variable, constant and/or decreasing resistance. It is contemplated that sections 32, 34, 36 can be variously dimensioned, for example, with regard to length, width, diameter and thickness. It is further contemplated that the respective cross-section of sections 32, 34, 36 may have various configurations, for example, round, oval, rectangular, irregular, uniform and non-uniform. Section 32 may have a different cross-sectional area, geometry, material or material property such as strength, modulus or flexibility relative to section 34.

Intermediate section 36 may have a variable thickness t (FIG. 3) according to the requirements of the particular application. It is envisioned that thickness t of intermediate section 36 may be in a range of 1-10 mm, preferably in a range of 2-8 mm, and most preferably in a range of 3-5 mm. It is further envisioned that the cross-sectional geometry or area of intermediate section 36 can be uniform, non-uniform, consistent or variable.

It is envisioned that intermediate section 36 may be configured as a flexible joint having a wide, narrow, round or irregular configuration. It is further envisioned that intermediate section 36 can be variously configured and dimensioned with regard to size, shape, thickness, geometry and material. Intermediate section 36 may also have one or a plurality of elements connecting sections 32, 34 such as spaced apart portions, staggered patterns and mesh. Intermediate section 36 may be fabricated from the same or alternative material to sections 32, 34. Intermediate section 36 may also have a different cross-sectional area, geometry or material property such as strength, modulus and flexibility relative to sections 32, 34. Intermediate section 36 may be connected to sections 32, 34 using various methods and structure including molding of a continuous component, mechanical fastening, adhesive bonding and combinations thereof. It is envisioned that intermediate section 36 has a flexible hinge configuration, which can be offset forward or backward relative to a central axis of rod 30 to modify the flexibility or stiffness of the vertebral rod system. It is further envisioned that particular parameters may be selected to modulate the flexibility or stiffness of the vertebral rod system including the cross-sectional area (or thickness) of intermediate section 36, material modulus that may correlate to the hardness of bumper 50 discussed below, modification of porosity in a range of 0-30 percent which may include modification of void volume in a range of 10 microns-1 mm, as well as rod material properties. These parameters allow modification of the properties or performance of the vertebral rod system such as strength, durability, flexibility (or stiffness), overall profile and the ability to employ a percutaneous approach, for a particular application.

Intermediate section 36 includes a flexible joint member 37, which has a C-shaped configuration and defines a corresponding shaped arcuate inner surface 38 and an open end 40. It is contemplated that joint member 37 may have alternative configurations such as U-shaped, V-shaped or W-shaped. It is further contemplated that vertebral rod 30 may include one or a plurality of intermediate sections 36 spaced along the length of rod 30. In embodiments including a plurality of sections 36, the multiple sections 36 may be disposed in similar, or alternative orientations such as aligned, non-aligned, offset, open end facing or not facing vertebrae and alternate angular orientation.

Upper section 32 is disposed adjacent to an upper portion 42 of open end 40 and the transition defines a front face 43. Lower section 34 is disposed adjacent a lower portion 44 and the transition defines a front face 45. Inner surface 38 defines a cavity 46 and a first locking part, such as, for example, a post 48. Post 48 has a first portion 49a, which is cylindrical, and a second portion 49b, which has an increasing diameter as post 48 transitions into surface 38, as shown in FIG. 3.

Cavity 46 is configured for disposal of a resistance member, such as, for example, a bumper 50, as shown in FIGS. 4 and 5. Bumper 50 has an exterior surface 52 that defines a second locking part, such as, for example, an opening 54. Opening 54 has a first portion 55a configured for receipt of portion 49a, and a second portion 55b having an increasing diameter and being configured for receipt of portion 49b. Opening 54 receives post 48 for fixed mounting of bumper 50 with vertebral rod 30 to lock these components of the vertebral rod system in place. It is contemplated that portions 49a, 49b may be variously configured and dimensioned, and portions 55a, 55b correspondingly configured and dimensioned for reception thereof. Portions 49a, 49b may be uniform in configuration and dimension. It is envisioned that the first locking part may include one or a plurality of elements, may be variously disposed about intermediate section 36, or employ fastening elements and adhesives, with the second locking part being correspondingly configured for engagement therewith.

Bumper 50 is elastic and configured to provide variable resistance to movement of sections 32, 34 and 36. It is contemplated that bumper 50 can provide increasing, variable, constant and/or decreasing resistance. Bumper 50 is disposed within cavity 46 and engages surface 38 in a close fitting engagement. Bumper 50 can be variously configured with regard to size, shape, for example, round, oblong, rectangular, triangular, spherical, and irregular shapes. It is envisioned that bumper 50 has a hardness in the range of 20 Shore A to 55 Shore D, and preferably between 40 and 90 Shore A. The material of bumper 50 can be solid or porous, homogeneous or heterogeneous, single polymer or a blend/composite of more than one polymer. It is contemplated that the resiliency of bumper 50 can prevent creep and improve shape recovery of the vertebral rod system. It is envisioned that bumper 50 is configured to prevent and/or resist closing of open end 40. It is further envisioned that bumper 50 is secured in place with intermediate section 36, and desirably mechanically-secured therewith in a configuration to present migration and expulsion therefrom. In other embodiments, bumper 50 can be textured, encapsulated, adhesively bonded and/or over molded with vertebral rod 30. Bumper 50 can be inserted with cavity 46 for assembly, or formed in situ by, for example, a pouch, bag or balloon with the bumper configuration being inserted into cavity 46 and injected with a curable material. Bumper 50 can be oversized or overstuffed within cavity 46 such that bumper 50 is continuously maintained under compression even when cavity 46 is expanded at a maximum range of motion. It is envisioned that vertebral rod 30 may not include a resistance member and/or intermediate section 36 has a linear configuration, as will be described with regard to particular embodiments discussed below.

In a first orientation of vertebral rod 30, longitudinal axis a is disposed at an angle x relative to longitudinal axis b about joint member 37, as shown in FIG. 3. Angle x is desirably in a range of 135 degrees to less than 180 degrees, and most desirably in a range of 150 degrees to 160 degrees. Angle x may be equal to 180 degrees. It is contemplated that in the first orientation, no flexion or extension forces are applied to vertebral rod 30. As sections 32, 34, 36 move to a second orientation from the first orientation, flexion and/or extension forces are applied to vertebral rod 30. As such, bumper 50 engagingly interacts with intermediate section 36 in a configuration that provides increasing resistance to movement of sections 32, 34 from the first orientation to the second orientation. Movement of the components of the vertebral rod system between one or a plurality of orientations is contemplated and may include a range of increasing and decreasing levels of resistance of the components of the vertebral rod system.

In assembly, operation and use, the vertebral rod system is employed with a surgical procedure for treatment of a spinal disorder affecting a section of a spine of a patient, as discussed herein. The vertebral rod system may also be employed with other surgical procedures. In particular, the vertebral rod system is employed with a surgical procedure for treatment of a condition or injury of an affected section of the spine including vertebrae V, as shown in FIGS. 6 and 7. It is contemplated that the vertebral rod system is attached to vertebrae V for dynamic stabilization of the affected section of the spine to provide stability for healing and therapeutic treatment, while allowing a desirable range of motion or load-sharing capability.

In use, to treat the affected section of the spine, a medical practitioner obtains access to a surgical site including vertebra V in any appropriate manner, such as through incision and retraction of tissues. It is envisioned that the vertebral rod system may be used in any existing surgical method or technique including open surgery, mini-open surgery, minimally invasive surgery and percutaneous surgical implantation, whereby the vertebrae V is accessed through a mini-incision, or sleeve that provides a protected passageway to the area. Once access to the surgical site is obtained, the particular surgical procedure is performed for treating the spinal disorder. The vertebral rod system is then employed to augment the surgical treatment. The vertebral rod system can be delivered or implanted as a pre-assembled device or can be assembled in situ. The vertebral rod system may be completely or partially revised, removed or replaced, for example, replacing bumper 50 only, replacing rod 30 and bumper 50 and using the in-place fastening elements.

A first fastening element, such as, for example, fixation screw assembly 70 is configured to attach upper section 32 to vertebra $V_1$. A second fastening element, such as, for example, fixation screw assembly 71 is configured to attach lower section 34 to adjacent vertebra $V_2$. Pilot holes are made in vertebrae $V_1$, $V_2$ for receiving fixation screw assemblies 70, 71. Fixation screw assemblies 70, 71 include threaded bone engaging portions 72 that are inserted or otherwise connected to vertebrae $V_1$, $V_2$, according to the particular requirements of the surgical treatment. Fixation screw assemblies 70, 71 each have a head 74 with a bore, or through opening and a set screw 76, which is torqued on to sections 32, 34 to attach rod 30 in place with vertebrae V, as will be described.

Figure 7A:
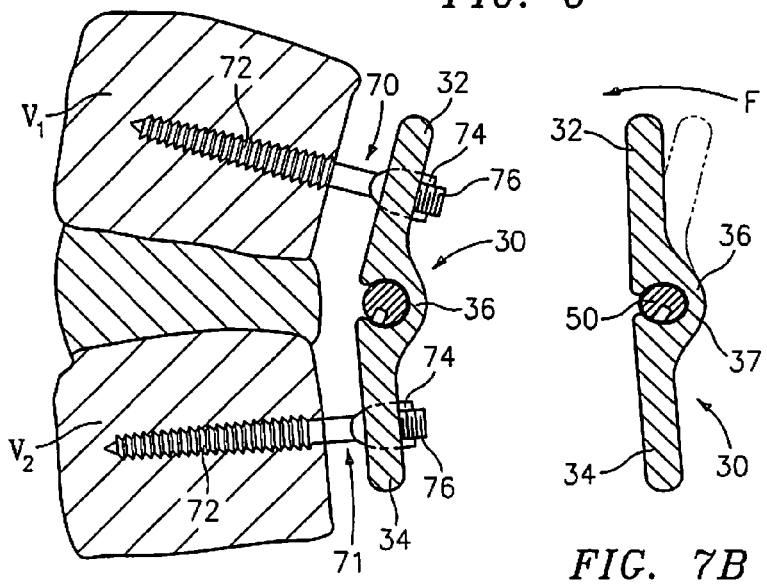
FIG. 7A is a lateral section view of the vertebral rod system of the present disclosure attached to vertebrae illustrating rod movement.

As shown in FIG. 6, the vertebral rod system includes two axially aligned and spaced rods 30, with portions of sections 32, 34 extending through the bores of heads 74. Set screws 76 of each head 74 are torqued on the end portions of rods 30 to securely attach rods 30 with vertebrae $V_1$, $V_2$. Upon fixation of the vertebral rod system with vertebrae V, vertebral rod 30 is configured to provide increasing resistance to movement of sections 32, 34 during flexion and extension of the spine. For example, vertebral rod 30, as shown in FIG. 7A, is in an unloaded or neutral state, which corresponds to the first orientation discussed above, where there is no appreciable tensile or compressive loads on the spinal motion segment comprising vertebrae $V_1$, $V_2$ and the intervertebral disc in between. In flexion and/or extension of the spinal motion segment caused by corresponding movement of the patient, rod 30 reacts with increasing resistance during movement of rod 30 to a second, third or more orientation(s).

Figure 7B:
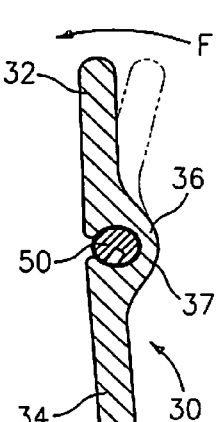
FIG. 7B is a lateral view of the vertebral rod system in cross section illustrating rod movement.
Figure 7C:
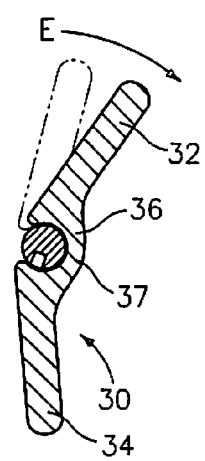
FIG. 7C is a lateral view of the vertebral rod system in cross section illustrating rod movement.

In flexion, as shown in FIG. 7B, upper section 32 moves relative to section 34, in the direction of arrow F. Joint member 37 flexibly compresses circumferentially about bumper 50 such that intermediate section 36 compresses bumper 50. This configuration increases resistance during flexion. In extension, as shown in FIG. 7C, upper section 32 moves relative to section 34, in the direction shown by arrow E. Joint member 37 flexibly expands circumferentially about bumper 50. Inner surface 38 adjacent to bumper 50 is in tension and the opposing edge of joint member 37 is in compression such that joint member 37 does not significantly compress bumper 50. Resistance is increased during extension. The increase of resistance during flexion and extension provides limited movement of vertebrae V for dynamic stabilization of the treated area of the spine. It is also contemplated that the rod 30 can be attached to the spinal motion segment in the reverse orientation such that the bumper 50 and the opening in the intermediate section face away from the spinal motion segment. In this case, the bumper 50 is under less compression during flexion and more compression during extension of the spinal motion segment.

The vertebral rod system can be used with various bone screws, pedicle screws or multi-axial screws (MAS) used in spinal surgery. It is contemplated that the vertebral rod system may be used with pedicle screws coated with an osteoconductive material such as hydroxyapatite and/or osteoinductive agent such as a bone morphogenic protein for enhanced bony fixation to facilitate motion of the treated spinal area. Rod 30 and bumper 50 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used, such as being disposed at the end portions of rod 30 and/or along the length thereof adjacent joint member 37 or with bumper 50.

Figures 8, 9, 10:
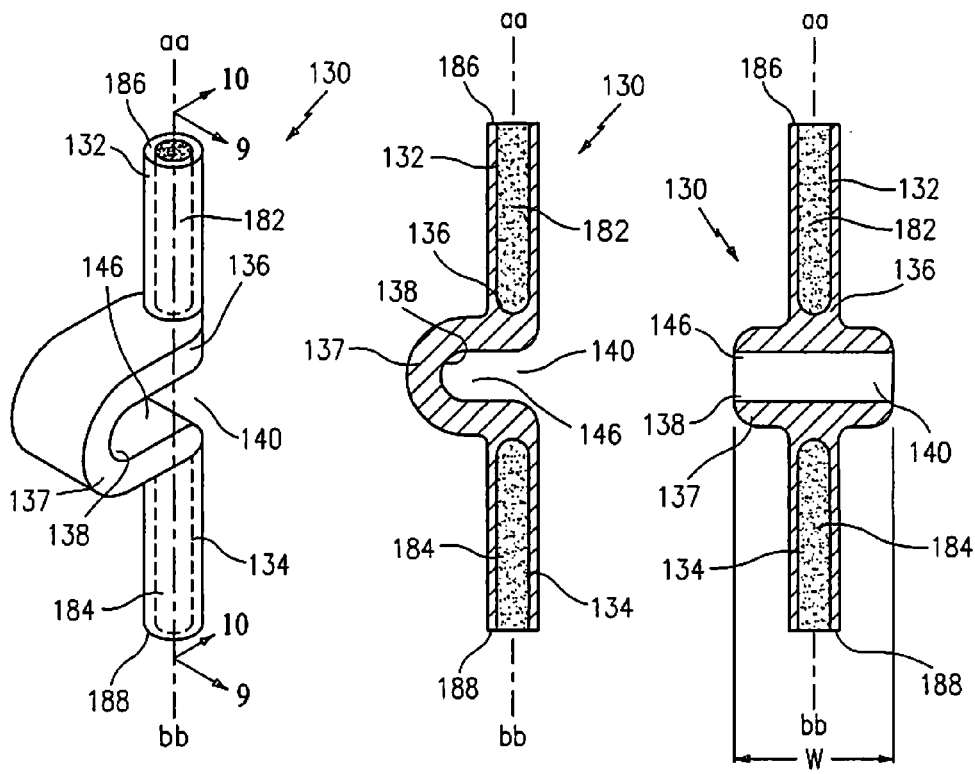
FIG. 8 is a side perspective view of an alternate embodiment of the vertebral rod shown in FIG. 2.
FIG. 9 is a side cross-section view of the vertebral rod taken along line 9-9 shown in FIG. 8.
FIG. 10 is a front cross-section view of the vertebral rod taken along line 10-10 shown in FIG. 8.

Referring to FIGS. 8-10, in an alternate embodiment similar to vertebral rod 30 described above, a vertebral rod 130 includes an upper section 132 that defines a longitudinal axis aa and a lower section 134 that defines a longitudinal axis bb. Upper section 132 includes a first material, such as, for example, an elongated core 182 having a first modulus of elasticity. Lower section 134 includes a second material, such as, for example, an elongated core 184 having a second modulus of elasticity. It is contemplated that the materials having the first and second modulus may be in a range of 10 to 400 GPa and preferably in a range of 50 to 250 GPa. It is further contemplated that the first material and the second material may have alternate, different or substantially equal modulus of elasticity.

Vertebral rod 130 is a composite dynamic or load-sharing device and sections 132, 134 each have a reinforced configuration based on the configuration of cores 182, 184 such that rod 130 has increased segmental rigidity and strength while achieving overall rod flexibility and durability during use. An outer layer 186 is disposed about core 182 and is formed of a material, such as those described herein, having a modulus of elasticity that is less than the first modulus of elasticity to provide flexibility and compliance to upper section 132. Outer layer 186 has a low modulus of elasticity relative to core 182 and surrounds core 182, which is formed of a material having a high modulus of elasticity to provide increased segmental stiffness and strength to vertebral rod 130 during a force/stress application, as will be described below.

An outer layer 188 is disposed about core 184 and is formed of a material having a modulus of elasticity that is less than the second modulus of elasticity to provide flexibility and compliance to lower section 134. Outer layer 188 has a low modulus of elasticity relative to core 184 and surrounds core 184, which is formed of a material having a high modulus of elasticity to provide increased stiffness and strength to vertebral rod 130 during a force/stress application. Cores 182, 184 can include a high modulus of elasticity material such as, for example, grade 5 titanium (Ti-6Al-4V), Commercially Pure Titanium (CP Ti), cobalt-chromium (Co—Cr), stainless steel, Nitinol, and/or carbon-reinforced polyetheretherketone PEEK, commercially pure titanium, titanium alloys, superelastic titanium alloys, cobalt-chrome alloys, stainless steel alloys and/or PEEK reinforced with long and/or continuous carbon fibers. Outer layers 186, 188 can include a low modulus material such as PEEK, PEEK reinforced with short and/or chopped carbon fibers, polyurethane, epoxy, CPT, and/or Nitinol. Outer layers 186, 188 may include a sleeve, coating or wrap disposed about cores 182, 184. Cores 182, 184 may extend along the entire rod section, or only a portion thereof. It is contemplated that cores 182, 184 may extend into an intermediate section 136 of vertebral rod 130, discussed below, and to an inner surface 138 of intermediate section 136. Sections 132, 134, 136 may include a material change along their respective length.

Other examples of materials used for higher modulus regions include cobalt-chrome alloys, titanium alloys, superelastic metallic alloys (e.g. Nitinol, super elasto-plastic metals, such as GUM METAL® manufactured by Toyotsu Material Incorporated of Japan), stainless steel alloys, continuous carbon fiber reinforced PEEK and/or short carbon fiber reinforced PEEK. Other examples of materials used for lower modulus regions include PEEK, short carbon fiber reinforced PEEK, continuous-carbon fiber reinforced PEEK, superelastic metallic alloys (e.g. Nitinol, super elasto-plastic metals, such as GUM METAL® manufactured by Toyotsu Material Incorporated of Japan), PEKK, polyurethane, polyethylene and/or polyphenylene.

The cross section configuration of each of cores 182, 184 may have alternate shapes such as round, oval, elliptical, oblong, square, rectangular, triangular, pentagonal and hexagonal. It is envisioned that each of cores 182, 184 may have a variable cross section along its length. The cores 182, 184 and/or outer layers 186, 188 may have machined surfaces, polished surfaces, smooth surfaces, textured surfaces, shot-peened surfaces, burnished surfaces, porous surfaces, patterned surfaces and wavy surfaces. The surfaces of cores 182, 184 and/or outer layers 186, 188 may be chemically treated or modified using various processes or materials which include oxidation, anodization, plasma treatment, vapor deposition, plating, coating and etching. It is contemplated that the vertebral rod may employ a heterogeneous composite, having a non-uniform carbon content.

Cores 182, 184 and/or outer layers 186, 188 may be located centrally or at an off-set distance from axes aa, bb of rod 130. It is contemplated that rod 130 may have a continuous or non-continuous core. Outer layers 186, 188 can be continuous, non-continuous, and/or provide complete or incomplete coverage of cores 182, 184. It is envisioned that outer layers 186, 188 can be solid or porous, for example, a solid sheath, a perforated sheath and a woven sheath. It is further envisioned that outer layers 186, 188 include a single material or a composite material, or may be of variable thickness around a core, and/or include a variable thickness along a core.

It is contemplated that, in a first orientation, longitudinal axis aa may be disposed at various angular orientations relative to longitudinal axis bb, such as, for example, those discussed herein. It is further contemplated that sections 132, 134 may include a laterally offset orientation, arcuate portion(s) and alternate lengths, such as, for example, those discussed herein. Movement of vertebral rod 130 between one or a plurality of orientations is envisioned and may include a range of increasing and decreasing levels of resistance. It is envisioned that sections 132, 134 can be bent, curved or deformed using a bending technique with or without heating. It is further envisioned that the respective core facilitates the desirable bending or deformed shape.

An intermediate section 136 is connected with sections 132, 134 and disposed therebetween as a joining section of the components of vertebral rod 130, similar to the intermediate sections discussed herein. Intermediate section 136 is formed of a third material having a third modulus of elasticity. The first modulus and the second modulus are each greater than the third modulus such that upper section 132 and lower section 134 provide a reinforced configuration of vertebral rod 130 and intermediate section 136 has a relatively flexible configuration. It is further contemplated that the first, second and third materials may have alternate, different or substantially equal modulus of elasticity.

Alternatively, intermediate section 136 may have a different shape, geometry or cross-section configuration relative to sections 132, 134. Intermediate section 136 may have an arcuate section, curvature or bend. Intermediate section 136 may have a C or U shaped to increase flexibility and fatigue resistance. Intermediate section 136 may have a substantially rectangular cross-section configuration to increase flexibility and fatigue resistance.

Intermediate section 136 has a low modulus of elasticity for flexibility relative to cores 182, 184, which are formed of a material having a high modulus of elasticity to provide increased segmental stiffness and strength to vertebral rod 130 during a force/stress application. Intermediate section 136 can include a low modulus material such as PEEK, short or chopped carbon fiber PEEK, PEEK with a low percentage of short and/or chopped carbon fibers such as in a range of 1 to 10% PEEK only with no reinforcement and/or partially reinforced such that a non-continuous reinforcement is provided across the flexible portion of the intermediate section with a gradually decreasing reinforcement toward the middle of the intermediate section. It is contemplated that intermediate section 136 is fully reinforced such that a continuous reinforcement is disposed across the flexible portion of the intermediate section.

Intermediate section 136 includes a flexible joint member 137, which has a U-shaped configuration and defines corresponding shaped arcuate inner surface 138 and an open end 140. Open end 140 defines a spaced apart dimension of the gap or opening defined thereby, and defines the spaced apart region of intermediate section 136 disposed between sections 132, 134. It is envisioned that height of open end 140 may be in a range of 3-20 mm, preferably in a range of 3-15 mm, and most preferably in a range of 3-10 mm.

Sections 132, 134 each define a dimension of thickness. For example, section 132 defines an outside diameter that includes twice the thickness of outer layer 186 and the diameter of core 182. Section 134 defines an outside diameter that includes twice thickness of outer layer 188 and the diameter of core 184. It is envisioned that the outside diameter of sections 132, 134 may be in a range of 2-11 mm, preferably in a range of 2.5-9 mm, and most preferably in a range of 3-7 mm. It is contemplated that sections 132, 134 may have alternate geometric cross-section configurations, for example, elliptical, rectangular, polygonal, irregular, uniform and non-uniform.

Flexible joint member 137 is enlarged relative to sections 132, 134, as shown in FIG. 10, and defines a width w. It is envisioned that width w of flexible joint member 137 may be in a range of 3-20 mm, preferably in a range of 3-15 mm, and most preferably in a range of 3-10 mm. Flexible joint member 137 further defines a thickness and it is envisioned that thickness of flexible joint member 137 may be in a range of 1-10 mm, preferably in a range of 2-8 mm, and most preferably in a range of 2-6 mm. It is contemplated that flexible joint member 137 may have alternate geometric cross-section configurations, for example, round, oval, rectangular, polygonal, irregular, uniform and non-uniform.

Inner surface 138 defines a cavity 146 configured for disposal of a resistance member (not shown), such as, for example, those discussed herein. Intermediate section 136 and the resistance member may include locking parts, similar to those described herein, for locking these components in place. Vertebral rod 130 may be employed with a surgical procedure for treating a spinal disorder, similar to that discussed above. The vertebral rod system may be employed with pedicle-based dynamic spinal rods or devices, flexible composite rods, posterior transition devices, posterior load-sharing devices or spinal rods, and low-modulus spinal rods. It is contemplated that the vertebral rod system may be employed with minimally invasive applications, such as, for example, those employing rod section diameters approximating 4.75 mm and/or 5.5 mm.

Figure 11:
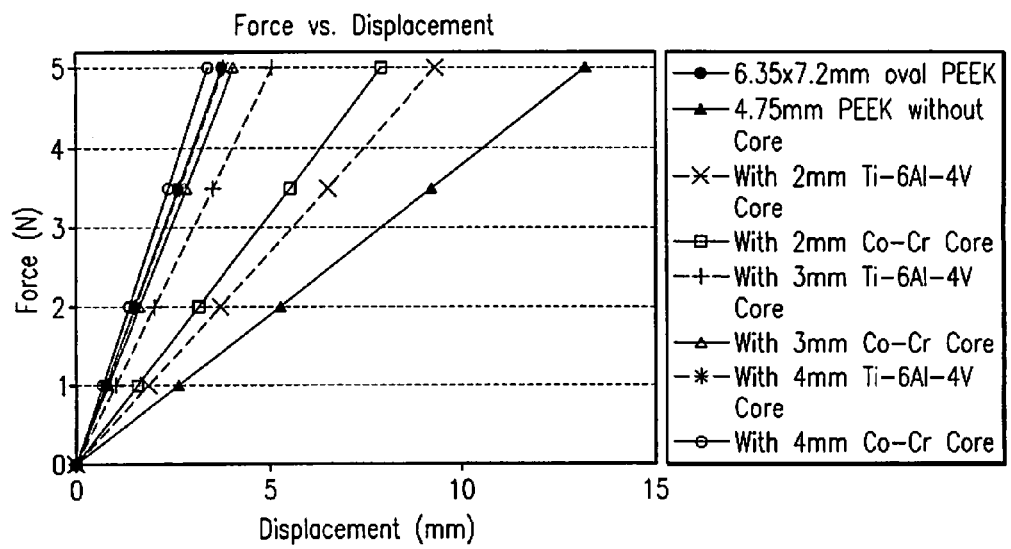
FIG. 11 is a graphical representation diagram of force vs. displacement for the vertebral rod shown in FIG. 8.

Referring to FIG. 11, a graphical diagram of force (N) vs. displacement (mm) illustrates calculated deflection of vertebral rod 130 under stress for alternate embodiments of cores 182, 184. As listed in the chart of the diagram shown in FIG. 11, cores 182, 184 can include alternate materials and thickness in accordance with the principles of the present disclosure. The data provided in FIG. 11 was obtained via computational modeling of PTD spinal rod stiffness cantilever beam loading for PEEK composite rods having a length of 100 mm and an outer diameter of 4.75 mm with various core materials and dimensions except when noted. In one example, sections 132, 134 have 4.75 mm cross section of a solid PEEK material having no metal core, which has a total deformation of approximately 13 mm over a stress application equivalent to 5 N. In another example, sections 132, 134 have 3 mm cores 182, 184 of Ti material, which has a total deformation of 5.1092 mm over a stress application equivalent to 5 N. In another example, sections 132, 134 have 3 mm cores 182, 184 of Co Cr material, which has a total deformation of 4.1128 mm over a stress application equivalent to 5 N. In another example, sections 132, 134 have 2 mm cores 182, 184 of Ti material, which has a total deformation of 9.3756 mm over a stress application equivalent to 5 N. In another example, sections 132, 134 have 2 mm cores 182, 184 of Co Cr material, which has a total deformation of 7.9513 mm over a stress application equivalent to 5 N. In another example, sections 132, 134 have 4 mm cores 182, 184 of Ti material, which has a total deformation of 3.8496 mm over a stress application equivalent to 5 N. In another example, sections 132, 134 have 4 mm cores 182, 184 of Co Cr material, which has a total deformation of 3.4382 mm over a stress application equivalent to 5 N. In another example, sections 132, 134 have oval cross section (6.35 mm by 7.2 mm) of solid PEEK material no metal core, which has a total deformation of 3.7873 mm over a stress application equivalent to 5 N. In another example of calculated deflection obtained via computational modeling and not shown in FIG. 11, sections 132, 134 have 3.5 mm cores 182, 184 of Co Cr material, which has a total deformation of 3.4118 mm over a stress application equivalent to 5 N. In another example of calculated deflection obtained via computational modeling and not shown in FIG. 11, sections 132, 134 have 3.5 mm cores 182, 184 of Ti material, which has a total deformation of 4.0521 mm over a stress application equivalent to 5 N.

In an alternative embodiment, sections 132, 134 may be made of composite materials such as a Co—Cr core disposed within a PEEK sleeve or outer layer or coating with a flexible intermediate section 136 of a lower modulus material such as PEEK, with a material change along the rod length and rod cross section.

In another embodiment, sections 132, 134 are made of high modulus materials such as Co—Cr or Ti-6Al-4V or long and/or continuous carbon fiber PEEK, and the flexible intermediate section 136 is made of a composite material such as a Co—Cr core or Ti-6Al-4V core in a PEEK sleeve with a material change along the rod length, and along the rod cross-section.

In another embodiment, sections 132, 134 are made of composite materials such as 30% short and/or chopped carbon fiber in PEEK, and flexible intermediate section 136 is made of a composite material such as 10% short carbon fiber in PEEK, with a change of carbon fiber content along the rod length.

Referring to FIGS. 12-14, in an alternate embodiment similar to vertebral rod 130 described above, a vertebral rod 230 includes an upper section 232 and a lower section 234. Upper section 232 includes an elongated core 282 having the first modulus of elasticity, and lower section 234 includes an elongated core 284 having a second modulus of elasticity, as described above.

Sections 232, 234 each have a reinforced configuration based on the configuration of cores 282, 284 such that vertebral rod 230 has increased rigidity and strength during use. An outer layer 286 is disposed about core 282 and is formed of a material having a modulus of elasticity that is less than the first modulus of elasticity to provide flexibility and compliance to upper section 232. Outer layer 286 has a low modulus of elasticity relative to core 282 and surrounds core 282, which is formed of a material having a high modulus of elasticity to provide increased stiffness and strength to vertebral rod 230.

An outer layer 288 is disposed about core 284 and is formed of a material having a modulus of elasticity that is less than the second modulus of elasticity to provide flexibility and compliance to lower section 234. Outer layer 288 has a low modulus of elasticity relative to core 284 and surrounds core 284, which is formed of a material having a high modulus of elasticity to provide increased stiffness and strength to vertebral rod 230.

An intermediate section 236 is connected with sections 232, 234 and disposed therebetween as a joining section of the components of vertebral rod 230. Intermediate section 236 includes a reinforcement portion, such as, for example, a core 290 formed of a material having a modulus of elasticity that is greater than the third modulus, discussed above. Core 290 has an arcuate configuration that conforms to the configuration of arcuate inner surface 238. Intermediate section 236 has an outer layer 292 formed of the third material having the third modulus of elasticity. Outer layer 292 has a low modulus of elasticity relative to core 290 and surrounds core 290, which is formed of a material having a high modulus of elasticity to provide increased stiffness and strength to vertebral rod 230 during a force/stress application. Outer layer 292 has a modulus of elasticity that is less than the modulus of elasticity of core 290 to provide flexibility and compliance to intermediate section 236.

The cross section configuration of core 290 may have alternate shapes such as round, oval, elliptical, oblong, square, rectangular, triangular, pentagonal and hexagonal. Core 290 may have a variable cross section along its length. Core 290 may have machined surface, polished surface, smooth surface, textured surface, shot-peened surface, burnished surface, porous surface, patterned surface and wavy surface. The surface of core 290 may be chemically treated or modified using various processes or materials which include oxidation, anodization, plasma treatment, vapor deposition, plating, coating and etching. Core 290 can be continuous or non-continuous. Outer layer 292 can be continuous, non-continuous and/or provide complete or incomplete coverage of core 290. Outer layer 292 can be solid or porous such as a solid sheath, a perforated sheath, a woven sheath and/or a sleeve configuration. It is contemplated that outer layer 292 may include a single material or a composite material, be of variable thickness around core 290, and/or be of variable thickness along core 290.

The modulus of elasticity of cores 282, 284 and 290 are equal and greater than the third modulus such that upper section 232, lower section 234 and intermediate section 236 provide a reinforced configuration of vertebral rod 230 with their respective outer layers providing flexibility and compliance. It is contemplated that the modulus of core 290 may be in a range of 10 to 400 GPa and preferably in a range of 50 to 250 GPa. It is further contemplated that the modulus of elasticity of cores 282, 284 and 290 may be alternate or substantially equal modulus of elasticity.

Core 290 connects cores 282 and 284 such that sections 232, 234 and 236 are in a continuous reinforcement configuration of vertebral rod 230. It is envisioned that cores 282, 284 and 290 may include partial reinforcement including a non-continuous high modulus material, such as intermittent or multiple sections and alternatively, may include complete reinforcement including continuous high modulus material.

Referring to FIGS. 15-17, in an alternate embodiment similar to vertebral rod 30 described above, a vertebral rod 330 includes an upper section 332 and a lower section 334. Upper section 332 includes a first material, such as, for example, an outer layer 386 having a first modulus of elasticity. Lower section 334 includes a second material, such as, for example, an outer layer 388 having a second modulus of elasticity. It is contemplated that the first and second modulus may be in a range of 10 to 400 GPa and preferably in a range of 50 to 250 GPa. It is further contemplated that the first material and the second material may be of alternate or substantially equal modulus of elasticity.

Vertebral rod 330 is a composite dynamic device and sections 332, 334 each have a reinforced configuration based on the configuration of outer layers 386, 388 such that vertebral rod 330 has increased rigidity and strength during use. Outer layer 386 is disposed about an elongated core 382, which is formed of a material, such as those described herein, having a modulus of elasticity that is less than the first modulus of elasticity to provide flexibility and compliance to upper section 332. Core 382 has a low modulus of elasticity relative to outer layer 386 and is disposed within outer layer 386, which is formed of a material having a high modulus of elasticity to provide increased stiffness and strength to vertebral rod 330 during a force/stress application.

Outer layer 388 is disposed about an elongated core 384 and is formed of a material having a modulus of elasticity that is less than the second modulus of elasticity to provide flexibility and compliance to lower section 334. Core 384 has a low modulus of elasticity relative to outer layer 388 and is disposed within outer layer 388, which is formed of a material having a high modulus of elasticity to provide increased stiffness and strength to vertebral rod 330 during a force/stress application. Outer layers 386, 388 can include a high modulus of elasticity material such as, for example, commercially pure titanium, titanium alloys, super-elastic titanium alloys, cobalt-chrome alloys, stainless steel alloys and/or PEEK reinforced with long and/or continuous carbon fibers. Cores 382, 384 can include a low modulus material such as PEEK and/or PEEK reinforced with short and/or chopped carbon fibers. Outer layers 386, 388 may include a sleeve, coating or wrap disposed about cores 382, 384.

The cross section configuration of outer layers 386, 388 may have alternate shapes such as round, oval, elliptical, oblong, square, rectangular, triangular, pentagonal and hexagonal. Outer layers 386, 388 may have variable cross sections along the length of rod 330. Outer layers 386, 388 may have machined surfaces, polished surfaces, smooth surfaces, textured surfaces, shot-peened surfaces, burnished surfaces, porous surfaces, patterned surfaces and wavy surfaces. The surface of outer layers 386, 388 may be chemically treated or modified using various processes or materials which include oxidation, anodization, plasma treatment, vapor deposition, plating, coating and etching. Outer layers 386, 388 can be continuous or non-continuous. Outer layers 386, 388 may provide continuous, non-continuous, complete or incomplete coverage of the cores. Outer layers 386, 388 may be solid or porous, for example, a solid sheath, a perforated sheath and a woven sheath. It is envisioned that outer layers 386, 388 may be a single material or a composite material, of variable thickness around the core and/or of variable thickness along the core.

An intermediate section 336, similar to intermediate section 136 described above, is connected with sections 332, 334 and disposed therebetween as a joining section of the components of vertebral rod 330, whereby upper section 332 and lower section 334 provide a reinforced configuration of rod 330 and intermediate section 336 has a relatively flexible configuration.

Referring to FIGS. 18-27, alternate embodiments of vertebral rod 130 described above, are shown. As shown in FIG. 18, an alternate embodiment of vertebral rod 130 includes a first section 432 having a first elongated core 482 formed of a material having the first modulus of elasticity, described above and having a cross section extending from a first end 494 of first section 432 to inner surface 138 of intermediate section 136. The cross section of core 482 comprises an outer diameter $D_1$ of first section 432 adjacent first end 494, a tapered portion 496 and extending to a reduced diameter $D_2$, relative to outer diameter $D_o$, adjacent to inner surface 138. An outer layer 486 having a modulus of elasticity less than the first modulus of elasticity is disposed about tapered portion 496. As the thickness of core 482 decreases to inner surface 138, the thickness of outer layer 486 increases.

Vertebral rod 130 includes a second section 434 having a second elongated core 484 formed of a material having the second modulus of elasticity, described above, and having a cross section extending from a first end 496 of second section 434 to inner surface 138. The cross section of core 484 comprises an outer diameter $D_3$ of second section 434 adjacent first end 496, a tapered portion 498 with a reduced diameter $D_4$, relative to outer diameter $D_3$, adjacent to inner surface 138. An outer layer 488, having a modulus of elasticity less than the second modulus of elasticity, is disposed about tapered portion 496. As the thickness of core 484 decreases to inner surface 138, the thickness of outer layer 488 increases. This configuration provides increased flexibility and compliance adjacent intermediate section 136.

As shown in FIG. 19, another alternate embodiment of vertebral rod 130 includes section 132 having a core reinforcement 582 formed of a material having the first modulus of elasticity, described above and extending to at least partially within intermediate section 136. An outer layer 486 of section 132 and an outer layer 590 of intermediate section 136, each having a modulus of elasticity less than the first modulus of elasticity, are disposed about core reinforcement 582. Vertebral rod 130 also includes section 134 having a core reinforcement 584 formed of a material having the second modulus of elasticity, described above and extending to at least partially within intermediate section 136. An outer layer 488 of section 134 and outer layer 590, each having a modulus of elasticity less than the second modulus of elasticity, are disposed about core reinforcement 584. This configuration of vertebral rod 130 provides partial reinforcement into intermediate section 138.

As shown in FIG. 20, another alternate embodiment of vertebral rod 130 includes a reinforcement core 690, having a relatively high modulus of elasticity, is disposed within intermediate section 136. Reinforcement core 690 has an arcuate configuration and conforms to the shape of inner surface 138. An outer layer 692, having a low modulus of elasticity relative to core 690, is disposed about reinforcement core 690. Core 690 has a first end 693 spaced apart from core 182 and a second end 694 spaced apart from core 184 to provide partial reinforcement into intermediate section 138.

As shown in FIG. 21, another alternate embodiment of vertebral rod 130 includes cores 182, 184 having dovetail reinforcement connections 790, 792, having the first and second modulus of elasticity, respectively. Dovetail reinforcement connections 790, 792 are disposed adjacent opening 140 and connect sections 132, 134 to intermediate section 136, while providing increased strength and rigidity to vertebral rod 130.

As shown in FIG. 22, another alternate embodiment of vertebral rod 130 includes an intermediate section 836 having a linear configuration in axial alignment with axis aa, in the non stressed orientation. Intermediate section 836 is formed of a material having the third modulus of elasticity, as described above. As shown in FIG. 23, another alternate embodiment of vertebral rod 130 includes an intermediate section 936 having a linear configuration in axial alignment with axis aa, in the non stressed orientation. Intermediate section 936 is formed of a material having the third modulus of elasticity and includes a lateral protuberance 990 to enhance strength and rigidity. As shown in FIG. 24, another alternate embodiment of vertebral rod 130 includes an intermediate section 936A, which has a reduced curvature profile. An inner surface 938A of intermediate section 936A has an arcuate configuration such that a lateral protuberance 990A of intermediate section 936A enhances strength and rigidity of vertebral rod 130.

As shown in FIG. 25, an alternate embodiment of vertebral rod 330 described above with regard to FIGS. 15-17 includes an intermediate section 1036 having a linear configuration in axial alignment with axis aa, in the non stressed orientation. Intermediate section 1036 is formed of a material having the third modulus of elasticity, as described above. As shown in FIG. 26, another alternate embodiment of vertebral rod 130 includes an intermediate section 1136 having a linear configuration in axial alignment with axis aa, in the non stressed orientation. Cores 182, 184 extend in a uniform cross section to diverging leg portions extending to Intermediate section 1136. Intermediate section 1136 is formed of a material having the third modulus of elasticity, as described above.

As shown in FIG. 27, another alternate embodiment of vertebral rod 130 includes an intermediate section 1236 having a linear configuration in axial alignment with axis aa, in the non stressed orientation. Intermediate section 1236 is formed of a material having the third modulus of elasticity and includes a pair of opposing lateral protuberances 1290 to enhance strength and rigidity.

Referring to FIGS. 28 and 29, in an alternate embodiment similar to vertebral rod 130 described above, a vertebral rod 1330 includes an upper section 1332 and a lower section 1334. Upper section 1332 includes a first material 1390, which is a polymer composite such as carbon-PEEK or carbon-PEKK having a first modulus of elasticity. Lower section 1334 includes a second material 1392, which is a polymer composite such as carbon-PEEK or carbon-PEKK having a second modulus of elasticity. It is contemplated that the first and second modulus may be in a range of 2.5 to 100 GPa and preferably in a range of 5 to 50 GPa. It is further contemplated that the first material and the second material may have alternate or substantially equal modulus of elasticity.

Vertebral rod 1330 is a non uniform composite dynamic device and has a reinforced configuration based on the configuration of the first and second materials such that vertebral rod 1330 has increased rigidity and strength during use. Sections 1332, 1334 are highly reinforced with for example carbon fibers for improved stiffness and strength. An intermediate section 1336, similar to intermediate section 136 discussed above, is not reinforced or lightly reinforced for flexibility and compliance. Transitions zones 1337 are disposed between sections 1332, 1334 and intermediate section 1336. It is preferred that transition zones 1337 have gradual changes in reinforcement (e.g. percentage of carbon fiber) to induce gradual changes in modulus between sections 1332, 1334 and intermediate section 1336. Gradual changes in modulus are expected to minimize stress risers and potential for failures at transition zones 1337. It is contemplated that transition zones 1337 and/or intermediate section 1336 may include a uniform reinforcement with no gradual change.

Referring to FIGS. 30-33, alternate embodiments of vertebral rod 130 described above illustrate examples of multiple level composite rods with multiple flexible intermediate sections. It is envisioned that each of the intermediate sections may be alternately configured. For example, a first intermediate section may be more flexible than a second or third intermediate section due to differences in geometry, cross-sectional area or material composition. It is further envisioned that an intermediate section with higher flexibility may be used to support an unfused or motion-preserving level of a spine. As such, an intermediate section with higher stiffness may be used to support the fused level, where an optimal balance between stabilization and load-sharing is desirable. It is contemplated that the reinforcement material or core of the vertebral rod may be different for the screw engaging sections of the rod to provide a different stiffening effect to different sections of the rod. For example, an upper section of the rod may be reinforced with a 3.5 mm Co—Cr core, a flexible intermediate section may be reinforced with a 3.0 mm short and/or chopped carbon fiber reinforced PEEK, and a lower section may be reinforced with 2.5 mm Ti-6Al-4V.

As shown in FIG. 30, in an alternate embodiment similar to vertebral rod 130 described above, a vertebral rod 1430 includes an upper section 1432 and a mid section 1434. Upper section 1432 includes an elongated core 1482 having a first modulus of elasticity. Mid section 1434 includes an elongated core 1484 having a second modulus of elasticity. It is contemplated that the first and second modulus may be in a range of 0 to 400 GPa and preferably in a range of 50 to 250 GPa. It is further contemplated that the first material and the second material may have alternate or substantially equal modulus of elasticity.

An outer layer 1486 is disposed about core 1482 and is formed of a material, such as those described herein, having a modulus of elasticity that is less than the first modulus of elasticity to provide flexibility and compliance to upper section 1432. An outer layer 1488 is disposed about core 1484 and is formed of a material having a modulus of elasticity that is less than the second modulus of elasticity to provide flexibility and compliance to lower section 1434.

A first flexible intermediate section 1436, similar to intermediate section 136 described above, is connected with sections 1432, 1434 and disposed therebetween as a joining section of the components of vertebral rod 1430. Intermediate section 1436 is formed of a third material having a third modulus of elasticity. The first modulus and the second modulus are each greater than the third modulus such that upper section 1432 and mid section 1434 provide a reinforced configuration of rod 1430 and intermediate section 1436 has a relatively flexible configuration.

A third elongated section, such as, for example, a lower section 1490 includes a fourth material, such as, for example an elongated core 1492 having a fourth modulus of elasticity. The fourth modulus is greater than the third modulus such that lower section 1490 provides a reinforced configuration of rod 1430. An outer layer 1494 is disposed about core 1492 and is formed of a material, such as those described herein, having a modulus of elasticity that is less than the fourth modulus of elasticity to provide flexibility and compliance to lower section 1490. It is contemplated that the fourth modulus may be in a range of 10 to 400 GPa and preferably in a range of 50 to 250 GPa. It is further contemplated that the fourth material, the first material and the second material may have alternate or substantially equal modulus of elasticity.

A second flexible intermediate section 1496 is connected with sections 1434, 1490 and disposed therebetween as a joining section. Intermediate section 1496 has a linear configuration in axial alignment with sections 1434, 1490, in the non stressed orientation. Intermediate section 1496 is formed of a material having a modulus of elasticity lower than the fourth modulus. Section 1490 has a modulus greater than the modulus of intermediate section 1496 such that lower section

1490 provides a reinforced configuration of rod 1430 and intermediate section 1496 has a relatively flexible configuration. Intermediate section 1496 may be more or less flexible than intermediate section 1436 depending on the geometry, cross sectional area and material composition of the components of vertebral rod 1430.

Vertebral rod 1430, including intermediate section 1496 and lower section 1490, has an increased length providing the ability to extend over two or more intervertebral disc levels. It is contemplated that the configuration of the vertebral rod system may provide dynamic or flexible stabilization over a plurality of intervertebral levels, including treated and untreated vertebral and intervertebral levels. It is further contemplated that intermediate section 1496 and lower section 1490 provides a less flexible, or more rigid stabilization relative to other components of vertebral rod 1430. Vertebral rod 1430 may be cut or trimmed during a surgical procedure such that the size of vertebral rod 1430 can be modified according to patient needs or the particular requirements of a surgical treatment or medical practitioner. Vertebral rod 1430 may be provided in precurved configurations with various levels of curvature to fit anatomical variations. Alternatively, a straight or pre-curved vertebral rod 1430 can be bent or reshaped intraoperatively to fit specific patient anatomy.

In embodiments including multiple flexible intermediate sections, the multiple elongated and intermediate sections may be disposed in similar, or alternative orientations such as aligned, non-aligned, offset, open end facing or not facing vertebrae and alternate angular orientation. In an alternate embodiment, as shown in FIG. 30A, vertebral rod 1430 discussed above includes a first orientation whereby longitudinal axis aa is disposed at an angle of 180 degrees relative to longitudinal axis bb. It is contemplated that longitudinal axis aa may be disposed at other angular orientations relative to longitudinal axis bb.

Sections 1434, 1496, 1490 have an arcuate configuration and increased length providing the ability to extend over two or more intervertebral elements. Lower section 1490 may be cut or trimmed during a surgical procedure such that the size of vertebral rod 1430 can be modified according to patient needs or the particular requirements of a surgical treatment or medical practitioner. The arcuate configuration of sections 1434, 1496, 1490 has a radius of curvature rr. Desirably, the radius of curvature rr is in a range of 20-400 mm, preferably in a range of 50-200 mm, and most preferably in a range of 100-150 mm.

In another alternate embodiment, as shown in FIG. 31, vertebral rod 1430 discussed above includes a second flexible intermediate section 1596, which has a reduced curvature profile. An inner surface 1538 of intermediate section 1536 has an arcuate configuration such that a lateral protuberance 1590 of intermediate section 1596 enhances strength and rigidity of vertebral rod 1430. Intermediate section 1596 may be used for load sharing stabilization at the fusion level of a spine.

In another alternate embodiment, as shown in FIG. 32, vertebral rod 1430 includes a second flexible section 1696 having a pair of opposing lateral protuberances 1698 to enhance strength and rigidity of vertebral rod 1430. In another alternate embodiment, as shown in FIG. 33, vertebral rod 1430 includes a second flexible section 1796 having a lateral protuberance 1798 to enhance strength and rigidity of vertebral rod 1430.

In another alternate embodiment, vertebral rod 1430 has a first flexible intermediate section having a C or U shaped configuration, with a second flexible intermediate section having an equivalent profile. Both flexible intermediate sections are made of PEEK only. The upper and lower sections have a core made of higher modulus material such as Co—Cr or Ti-6Al-4V or long and/or continuous carbon fiber PEEK, and an outer sleeve disposed thereabout made of a lower modulus material PEEK. It is envisioned that the first flexible intermediate section may be relatively more flexible than the second flexible intermediate section due to its C or U shaped configuration. It is contemplated that the two separate flexible intermediate sections have the same material composition with different geometries.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A vertebral rod comprising:
a first elongated section;
a second elongated section; and
a first intermediate section disposed between the first section and the second section, the intermediate section having an arcuate inner surface that defines a cavity, the cavity including an open end having a width that is less than a maximum width of the cavity, the cavity further including a protrusion,
wherein the rod is movable between an unbiased configuration in which the first and second sections are non-coaxial and a biased configuration in which the first and second sections are coaxial, the protrusion extending parallel to one of the first and second sections and at an acute angle to the other of the first and second sections when the rod is in the unbiased configuration,
wherein the first section has a heterogeneous composite reinforced configuration comprising an outer layer and a core, the outer layer having a modulus of elasticity different from a modulus of elasticity of the core, the first section having a first modulus of elasticity, the second section has a heterogeneous composite reinforced configuration comprising an outer layer and a core, the outer layer of the second section having a modulus of elasticity different from a modulus of elasticity of the core of the second section, the second section having a second modulus of elasticity, the intermediate section comprising a third material having a third modulus of elasticity, the first modulus and the second modulus each being greater than the third modulus such that the first and second sections provide a reinforced configuration of the vertebral rod and the intermediate section has a relatively flexible configuration.

2. A vertebral rod according to claim 1, wherein the first modulus of elasticity is substantially equal to the second modulus of elasticity.

3. A vertebral rod according to claim 1, wherein the first modulus of elasticity is different from the second modulus of elasticity.

4. A vertebral rod according to claim 1, wherein the rod includes an elastomeric resistance member positioned within such that the resistance member engages the protrusion.

5. A vertebral rod according to claim 4, wherein the intermediate section has an arcuate configuration.

6. A vertebral rod according to claim 4, wherein the intermediate section has a C-shaped configuration and the resistance member prevents the open end from closing.

7. A vertebral rod according to claim 4, wherein the first section, the second section and the intermediate section each comprise polyetheretherketone (PEEK) and the resistance member comprises silicone.

8. A vertebral rod according to claim 4, wherein the first section, the second section and the intermediate section each consist of polyetheretherketone (PEEK) and the resistance member consists of silicone.

9. A vertebral rod according to claim 1, wherein the first material is an elongated core having a cross section extending from a first end of the first section to the inner surface of the intermediate section, the core cross section comprising an outer diameter of the first section adjacent the first end and including a tapered portion with a reduced diameter, relative to the outer diameter, adjacent the inner surface.

10. A vertebral rod according to claim 9, wherein the second material is an elongated core having a cross section extending from a first end of the second section to the inner surface of the intermediate section, the core cross section of the second section comprising an outer diameter of the second section adjacent the first end of the second section and including a tapered portion with a reduced diameter, relative to the outer diameter of the second section, adjacent the inner surface.

11. A vertebral rod according to claim 1, wherein the first and second elongated sections are each a polymer composite including carbon fiber concentration.

12. A vertebral rod according to claim 1, further comprising a third elongated section including a fourth material having a fourth modulus of elasticity; and a second flexible intermediate section disposed between the second section and the third section, wherein the fourth modulus is greater than the third modulus.

13. A vertebral rod according to claim 12, wherein the second intermediate section includes a lateral protuberance.

14. A vertebral rod comprising:
a first elongated section;
a second elongated section;
a first flexible intermediate section disposed between the first section and the second section having an arcuate inner surface that defines a cavity, the cavity including an open end having a width that is less than a maximum width of the cavity, the cavity further including a protrusion;
a resistance member positioned in the cavity such that the resistance member engages the protrusion to retain the resistance member in the cavity;
a third elongated section; and
a second flexible intermediate section disposed between the second section and the third section,
wherein the rod is movable between an unbiased configuration in which the first and second sections are non-coaxial and a biased configuration in which the first and second sections are coaxial, the protrusion extending parallel to one of the first and second sections and at an acute angle to the other of the first and second sections when the rod is in the unbiased configuration.

15. A vertebral rod according to claim 14, wherein the first elongated section has a heterogeneous composite reinforced configuration comprising an outer layer and a core, the outer layer being formed of a material having a modulus of elasticity that is less than a modulus of elasticity of the core, the first elongated section having a first modulus of elasticity, the second elongated section having a heterogeneous composite reinforced configuration comprising an outer layer and a core, the outer layer of the second section being formed of a material having a modulus of elasticity that is less than a modulus of elasticity of the core of the second section, the second elongated section having a second modulus of elasticity, the first flexible intermediate section comprising a heterogeneous composite reinforced configuration having a core and an outer layer disposed about the core, the outer layer of the first flexible intermediate section having a modulus of elasticity different from a modulus of elasticity of the core of the first flexible intermediate section, the first flexible intermediate section having a third modulus of elasticity, wherein the first modulus and the second modulus are each greater than the third modulus such that the first and second sections provide a reinforced configuration of the vertebral rod and the first flexible intermediate section has a relatively flexible configuration, the third elongated section having a heterogeneous composite reinforced configuration comprising an outer layer and a core, the outer layer of the third section being formed of a material having a modulus of elasticity that is less than the modulus of elasticity of the core of the third section, the third elongated section having a fourth modulus of elasticity, the fourth modulus being greater than the third modulus.

* * * * *